(12) United States Patent
Jacobson et al.

(10) Patent No.: US 10,688,111 B2
(45) Date of Patent: *Jun. 23, 2020

(54) LIQUID FORMULATIONS OF COMPOUNDS ACTIVE AT SULFONYLUREA RECEPTORS

(71) Applicant: Biogen Chesapeake LLC, Cambridge, MA (US)

(72) Inventors: Sven Jacobson, New York, NY (US); Gillian Clarke, Middlesex (GB); Rajinder Matharu, Bloomington, IN (US)

(73) Assignee: Biogen Chesapeake LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/094,461

(22) Filed: Apr. 8, 2016

(65) Prior Publication Data

US 2017/0216321 A1 Aug. 3, 2017

Related U.S. Application Data

(63) Continuation of application No. 12/863,525, filed as application No. PCT/US2009/032455 on Jan. 29, 2009, now abandoned.

(60) Provisional application No. 61/024,499, filed on Jan. 29, 2008.

(51) Int. Cl.
| | |
|---|---|
| *A61K 31/64* | (2006.01) |
| *A61K 47/18* | (2017.01) |
| *A61K 9/08* | (2006.01) |
| *A61K 47/26* | (2006.01) |
| *A61K 47/10* | (2017.01) |
| *A61K 9/00* | (2006.01) |

(52) U.S. Cl.
CPC ............ *A61K 31/64* (2013.01); *A61K 9/0019* (2013.01); *A61K 9/08* (2013.01); *A61K 47/10* (2013.01); *A61K 47/18* (2013.01); *A61K 47/26* (2013.01)

(58) Field of Classification Search
CPC ........ A61K 31/64; A61K 47/10; A61K 47/18; A61K 9/08; A61K 47/26; A61K 9/0019
See application file for complete search history.

(56) References Cited

U.S. PATENT DOCUMENTS

| | | | | |
|---|---|---|---|---|
| 5,258,185 | A | * 11/1993 | Bauer | A61K 9/146 424/439 |
| 5,856,360 | A | 1/1999 | Salzman et al. | |
| 5,977,109 | A | 11/1999 | Nakakura et al. | |
| 6,056,977 | A | * 5/2000 | Bhagwat | A61K 9/2018 424/458 |
| 6,537,578 | B1 | 3/2003 | Bhagwat et al. | |
| 8,277,845 | B2 | 10/2012 | Jacobson | |
| 8,858,997 | B2 | 10/2014 | Jacobson | |
| 2003/0125338 | A1 | 7/2003 | Connop | |
| 2003/0215889 | A1 | 11/2003 | Simard et al. | |
| 2005/0053653 | A1 | * 3/2005 | Kidane | A61K 9/0004 424/463 |
| 2006/0100183 | A1 | 5/2006 | Simard et al. | |
| 2006/0183803 | A1 | 8/2006 | Hevia et al. | |
| 2006/0189663 | A1 | 8/2006 | Holm | |
| 2006/0276411 | A1 | 12/2006 | Simard et al. | |
| 2007/0249583 | A1 | 10/2007 | Stein | |
| 2008/0220441 | A1 | 9/2008 | Birnbaum | |
| 2009/0233995 | A1 | 9/2009 | Lautt | |
| 2010/0056444 | A1 | 3/2010 | Jacobsen et al. | |

FOREIGN PATENT DOCUMENTS

| | | | |
|---|---|---|---|
| WO | WO 9906024 A1 * | 2/1999 | ........... A61K 9/1075 |
| WO | WO 2002/079778 A2 | 10/2002 | |
| WO | WO 2003/063825 A1 | 8/2003 | |
| WO | WO 2008/038126 A2 | 4/2008 | |

OTHER PUBLICATIONS

Wikipedia entry for mannitol (retrieved Apr. 26, 2018) (Year: 2018).*
Pablo Estevez et al., Development and stability study of glibenclamide oral liquid paediatric formulations for the treatment of permanent neonatal diabetes mellitus, Eur J Hosp Pharm 2016;23:213-218. doi:10.1136/ejhpharm-2015-000763 (Year: 2016).*
Chen, et al., "Cell swelling and a nonselective cation channel regulated by internal Ca2 + and ATP in native reactive astrocytes from adult rat brain", The Journal of Neuroscience, 21(17): 6512-6521' (2001).
Chen, et al., "Functional coupling between sulfonylurea receptor type 1 and a nonselective cation channel in reactive astrocytes from adult rat brain", The Journal of Neuroscience, 23(24): 8568-8577, (2003).

(Continued)

*Primary Examiner* — Sarah Pihonak
*Assistant Examiner* — Jason Deck
(74) *Attorney, Agent, or Firm* — Rothwell, Figg, Ernst & Manbeck, P.C.

(57) ABSTRACT

The invention provides liquid formulations of compounds that act at sulfonylurea receptors that are suitable for intravenous and intra-arterial infusion. Compounds active at a sulfonylurea receptor include glibenclamide, tolbutamide, repaglinide, nateglinide, meglitinide, midaglizole, LY397364, LY389382, glyclazide, and glimepiride. Liquid formulations may be concentrated solutions suitable for storage; may be diluted (e.g., dilution of 1:1 or 1:1.2) suitable for bolus injections, and may be further diluted (e.g., dilution of 1:10 or 1:20 or more) for intravenous and intra-arterial infusion over an extended period of time. For example, a liquid formulation may include at least about 0.05 mg/ml glibenclamide in a water-based solution including 40% polyethylene glycol 300, 10% Ethanol, 50% water, at about pH 9. The solution may include a buffer, and is suitable for storage in refrigerator or at room temperature. This solution may be diluted 1:1, or more (e.g., 1:20) without precipitation of the glibenclamide.

24 Claims, 12 Drawing Sheets

(56) References Cited

OTHER PUBLICATIONS

Gardiner, et al., "Regional haemodynamic responses to infusion of lipopolysaccharide in conscious rats: effects of pre-or post-treatment with glibenclamide", British Journal of Pharmacology, 128: 1772-1778, (1999).

Gold, et al., "Intra-septal injections of glucose and glibenclamide attenuate galanin-induced spontaneous alternation performance deficits in the rat", Brain Research, 813: 50-56, (1998).

Junquero, et al., "Pharmacological profile ofF 12511, (S)-2', 3', 5'-trimethyl-4'-hydroxy-adodecylthioacetanilide a powerful and systemic acylcoenzyme A: cholesterol acyltransferase inhibitor", Biochemical Pharmacology, 61: 97-108, (2001).

M. R. Stefani, P. E. Gold, Brain Research, 1998, 813, 50-56.

M.A. El-Massik, I.A. Darwish, E. E. Hassan, L.K. Ei-Khordagui, Development of a dissolution medium for glibenclamide, International Journal of Pharmaceutics 140 (1996) 69-76.

Rajendran SO, BK Philip, R Gopinath, B Suresh, RPHPLC method for the estimation of glibenclamide in human serum, 2007, 69, 6, 796-799.

S. Galal, M. El Massik, 0. Abdallah, N. Daabis, Acta Pharm. 2003, 53, 57-64.

Sano, et al., "Preventing Alzheimer's disease: Separating fact from fiction", CNS Drugs, vol. 22, pp. 887-902, (2008).

Simard, et al., "Non-selective cation channels, transient receptor potential channels and ischemic stroke", Biochimica et Biophysica Acta, 1772: 947-957, (2007).

Tanaka, et al., "Inhibitors of Acyl-CoA: Cholesterol 0-Acyltransferase. 2. Identification and structure-Activity relationships of a novel series of N-Alk 1-N-(heteroaryl-substituted benzyl)-Narylureas", J. Med. Chern., 41: 2390-2410, (1998).

Vanelli, et al., "Cardiovascular responses to glibenclamide during endotoxaemia in the pig", Veterinary Research Communications, 21: 187-200, ( 1997).

* cited by examiner

Figure 3A    Stability of Glibenclamide Injections

Glibenclamide 1mg/ml, pH 9, Meglumine 5mM   2-8°C

| Timepoint/Condition | Glibenclamide assay by SAP385 (mg/ml) | Related substances by SAP385 (% w/w) | | | | | | A/N |
|---|---|---|---|---|---|---|---|---|
| | | 0.11 | 0.11 | 0.18 Imp A | 0.21 | 0.28 Imp B | 0.40 | 1.00 Glibenclamide | Total ≥0.05% | |
| Initial | 1.018 | 0.02 | 0.01 | 0.10 | nd | 0.13 | tr | 99.76 | 0.22 | 062080 |
| 1 month at 2-8°C | 1.011 | nd | nd | 0.10 | nd | 0.17 | nd | 99.74 | 0.26 | 070066 |
| 2 months at 2-8°C | | | | | | | | | | |
| 3 months at 2-8°C | | | | | | | | | | |

| Timepoint/Condition | Appearance and Particulates (SAP009) | pH (SAP004) | A/N |
|---|---|---|---|
| Initial | Clear colourless liquid with some fibres but no particulates believed to be drug-related. | 8.76, 8.82 Mean = 8.79 | 062080 |
| 1 month at 2-8°C | Clear colourless liquid, free from visible particles. | 8.25, 8.27 Mean = 8.26 | 070066 |

Stability of Glibenclamide Injections

Figure 3B

Glibenclamide 1mg/ml, pH 9, Meglumine 5mM 25°C/60% RH

| Timepoint/Condition | Glibenclamide assay by SAP385 (mg/ml) | Related substances by SAP385 (% w/w) | | | | | | | |
|---|---|---|---|---|---|---|---|---|---|
| | | 0.11 | 0.11 | 0.15 | 0.18 Imp A | 0.21 | 0.28 Imp B | 0.40 | 1.00 Glibenclamide | Total ≥0.05% | A/N |
| Initial | 1.018 | 0.02 | 0.01 | nd | 0.10 | nd | 0.13 | tr | 99.76 | 0.22 | 062080 |
| 1 month at 25°C/60% RH | 0.999 | nd | nd | 0.27 | 0.21 | nd | 0.15 | nd | 99.38 | 0.62 | 070067 |
| 2 months at 25°C/60% RH | | | | | | | | | | | |
| 3 months at 25°C/60% RH | | | | | | | | | | | |

| Timepoint/Condition | Appearance and Particulates (SAP009) | pH (SAP004) | A/N |
|---|---|---|---|
| Initial | Clear colourless liquid with some fibres but no particulates believed to be drug-related. | 8.76, 8.82 Mean = 8.79 | 062080 |
| 1 month at 25°C/60% RH | Clear colourless liquid, free from visible particles. | 7.42, 7.39 Mean = 7.40 | 070067 |

Stability of Glibenclamide Injections

Figure 3C

Glibenclamide 1mg/ml, pH 9, Meglumine 5mM 40°C/75% RH

| Timepoint/Condition | Glibenclamide assay by SAP385 (mg/ml) | Related substances by SAP385 (% w/w) | | | | | | | | | A/N |
|---|---|---|---|---|---|---|---|---|---|---|---|
| | | 0.11 | 0.11 | 0.15 | 0.15 | 0.18 Imp A | 0.20 | 0.21 | 0.28 Imp B | 0.40 | 0.58 | 1.00 Glibenclamide | Total ≥0.05% | |
| Initial | 1.018 | 0.11 | 0.11 | nd | 0.15 | 0.18 | nd | 0.21 | 0.28 | 0.40 | nd | 99.76 | 0.22 | 062080 |
| 1 month at 40°C/75% RH | 0.917 | 0.02 | 0.01 | nd | 0.19 | 2.82 | 0.06 | 0.26 | 0.13 | 1.01 | 0.30 | 95.11 | 4.82 | 070068 |
| 2 months at 40°C/75% RH | | 0.07 | nd, 0.04 | 0.06 | | 0.10 | | | 0.13 | tr | | | | |
| 3 months at 40°C/75% RH | | | | | | | | | | | | | | |

| Timepoint/Condition | Appearance and Particulates (SAP009) | pH (SAP004) | A/N |
|---|---|---|---|
| Initial | Clear colourless liquid with some fibres but no particulates believed to be drug-related. | 8.76, 8.82 Mean = 8.79 | 062080 |
| 1 month at 40°C/75% RH | Clear colourless liquid, free from visible particles. | 7.19, 7.19 Mean = 7.19 | 070068 |

Stability of Glibenclamide Injections

Figure 3D

Glibenclamide 1mg/ml, pH 9, Diethanolamine 5mM  2-8°C

| Timepoint/ Condition | Glibenclamide assay by SAP385 (mg/ml) | Related substances by SAP385 (% w/w) | | | | | |
|---|---|---|---|---|---|---|---|
| | | 0.11 | 0.18 Imp A | 0.21 | 0.28 Imp B | 0.40 | 1.00 Glibenclamide | Total ≥0.05% | A/N |
| Initial | 0.994 | 0.11 | 0.18 Imp A | 0.21 | 0.28 Imp B | 0.40 | 1.00 Glibenclamide |  |  |
| Initial | 0.994 | 0.01 | 0.09 | nd | 0.12 | 0.04 | 99.73 | 0.21 | 062081 |
| 1 month at 2-8°C | 0.985 | | | Not tested | | | | | 070069 |
| 2 months at 2-8°C | | | | | | | | | |
| 3 months at 2-8°C | | | | | | | | | |

| Timepoint/ Condition | Appearance and Particulates (SAP009) | pH (SAP004) | A/N |
|---|---|---|---|
| Initial | Clear colourless liquid with some fibres but no particulates believed to be drug-related. | 9.02, 9.05 Mean = 9.03 | 062081 |
| 1 month at 2-8°C | Clear colourless liquid, free from visible particles. | 8.72, 8.74 Mean = 8.73 | 070069 |

Stability of Glibenclamide Injections

Figure 3E

Glibenclamide 1mg/ml, pH 9, Diethanolamine 5mM  25°C/60% RH

| Timepoint/Condition | Glibenclamide assay by SAP385 (mg/ml) | Related substances by SAP385 (% w/w) | | | | | | A/N |
|---|---|---|---|---|---|---|---|---|
| | | 0.11 | 0.18 Imp A | 0.21 | 0.28 Imp B | 0.40 | 1.00 Glibenclamide | Total ≥0.05% | |
| Initial | 0.994 | 0.11 | 0.09 | nd | 0.12 | 0.04 | 99.73 | 0.21 | 062081 |
| 1 month at 25°C/60% RH | 0.984 | 0.01 | 0.02 | | | | | | 070070 |
| 2 months at 25°C/60% RH | | | | Not tested | | | | | |
| 3 months at 25°C/60% RH | | | | | | | | | |

| Timepoint/Condition | Appearance and Particulates (SAP009) | pH (SAP004) | A/N |
|---|---|---|---|
| Initial | Clear colourless liquid with some fibres but no particulates believed to be drug-related. | 9.02, 9.05 Mean = 9.03 | 062081 |
| 1 month at 25°C/60% RH | Clear colourless liquid, free from visible particles. | 8.51, 8.50 Mean = 8.51 | 070070 |

Stability of Glibenclamide Injections

Figure 3F

Glibenclamide 1mg/ml, pH 9, Diethanolamine 5mM 40°C/75% RH

| Timepoint/ Condition | Glibenclamide assay by SAP385 (mg/ml) | Related substances by SAP385 (% w/w) | | | | | |
|---|---|---|---|---|---|---|---|
| | | | 0.18 Imp A | 0.28 Imp B | 0.40 | 1.00 Glibenclamide | Total ≥0.05% | A/N |
| Initial | 0.994 | 0.11 | | 0.21 | | | | 062081 |
| 1 month at 40°C/75% RH | 0.972 | 0.01 | 0.09 | 0.12 | 0.04 | 99.73 | 0.21 | 070071 |
| 2 months at 40°C/75% RH | | | | Not tested | | | | |
| 3 months at 40°C/75% RH | | | | | | | | |

| Timepoint/ Condition | Appearance and Particulates (SAP009) | pH (SAP004) | A/N |
|---|---|---|---|
| Initial | Clear colourless liquid with some fibres but no particulates believed to be drug-related. | 9.02, 9.05 Mean = 9.03 | 062081 |
| 1 month at 40°C/75% RH | Clear colourless liquid, free from visible particles. | 8.27, 8.24 Mean = 8.25 | 070071 |

Stability of Glibenclamide Injections

Figure 3G

Glibenclamide 1mg/ml, pH 9.5, Meglumine 10mM 2-8°C

| Timepoint/ Condition | Glibenclamide assay by SAP385 (mg/ml) | Related substances by SAP385 (% w/w) | | | | | | | Total ≥0.05% | A/N |
|---|---|---|---|---|---|---|---|---|---|---|
| | | 0.11 | 0.11 | 0.18 Imp A | 0.21 | 0.28 Imp B | 0.40 | 1.00 Glibenclamide | | |
| Initial | 1.001 | 0.01 | nd | 0.10 | nd | 0.13 | Tr. 0.05 | 99.74 | 0.25 | 062082 |
| 1 month at 2-8°C | 0.999 | Not tested | | | | | | | | 070072 |
| 2 months at 2-8°C | | | | | | | | | | |
| 3 months at 2-8°C | | | | | | | | | | |

| Timepoint/ Condition | Appearance and Particulates (SAP009) | pH (SAP004) | A/N |
|---|---|---|---|
| Initial | Clear colourless liquid with some fibres but no particulates believed to be drug-related. | 8.72, 8.71 Mean = 8.71 | 062082 |
| 1 month at 2-8°C | Clear colourless liquid, free from visible particles | 8.35, 8.34 Mean = 8.35 | 070072 |

Stability of Glibenclamide Injections

Figure 3H

Glibenclamide 1mg/ml, pH 9.5, Meglumine 10mM 25°C/60% RH

| Timepoint/ Condition | Glibenclamide assay by SAP385 (mg/ml) | Related substances by SAP385 (% w/w) | | | | | | | Total ≥0.05% | A/N |
|---|---|---|---|---|---|---|---|---|---|---|
| | | 0.11 | 0.11 | 0.18 Imp A | 0.21 | 0 28 Imp B | 0.40 | 1.00 Glibenclamide | | |
| Initial | 1.001 | 0.01 | nd | 0.10 | nd | 0.13 | Tr, 0.05 | 99.74 | 0.25 | 062082 |
| 1 month at 25°C/60% RH | 0.993 | Not tested | | | | | | | | 070073 |
| 2 months at 25°C/60% RH | | | | | | | | | | |
| 3 months at 25°C/60% RH | | | | | | | | | | |

| Timepoint/ Condition | Appearance and Particulates (SAP009) | pH (SAP004) | A/N |
|---|---|---|---|
| Initial | Clear colourless liquid with some fibres but no particulates believed to be drug-related. | 8.72, 8.71 Mean = 8.71 | 062082 |
| 1 month at 25°C/60% RH | Clear colourless liquid, free from visible particles. | 7.81, 7.80 Mean = 7.80 | 070073 |

Stability of Glibenclamide Injections

Figure 3I

Glibenclamide 1mg/ml, pH 9.5, Meglumine 10mM  40°C/75% RH

| Timepoint/ Condition | Glibenclamide assay by SAP385 (mg/ml) | Related substances by SAP385 (% w/w) | | | | | | | | A/N |
|---|---|---|---|---|---|---|---|---|---|---|
| | | 0.11 | 0.11 | 0.18 Imp A | 0.21 | 0.28 Imp B | 0.40 | 1.00 Glibenclamide | Total ≥0.05% | |
| Initial | 1.001 | 0.01 | nd | 0.10 | nd | 0.13 | Tr. 0.05 | 99.74 | 0.25 | 062082 |
| 1 month at 40°C/75% RH | 0.975 | Not tested | | | | | | | | 070074 |
| 2 months at 40°C/75% RH | | | | | | | | | | |
| 3 months at 40°C/75% RH | | | | | | | | | | |

| Timepoint/ Condition | Appearance and Particulates (SAP009) | pH (SAP004) | A/N |
|---|---|---|---|
| Initial | Clear colourless liquid with some fibres but no particulates believed to be drug-related. | 8.72, 8.71 Mean = 8.71 | 062082 |
| 1 month at 40°C/75% RH | Clear colourless liquid, free from visible particles. | 7.58, 7.58 Mean = 7.58 | 070074 |

Stability of Glibenclamide Injections

Figure 3J

Glibenclamide 1mg/ml, Non-aqueous formulation - 25°C/60% RH

| Timepoint/ Condition | Glibenclamide assay by SAP385 (mg/ml) | Related substances by SAP385 (% w/w) | | | | | | | | A/N |
|---|---|---|---|---|---|---|---|---|---|---|
| | | 0.11 | 0.11 | 0.18 Imp A | 0.21 | 0.28 Imp B | 0.40 | 1.00 Glibenclamide | Total ≥0.05% | |
| Initial | 0.997 | 0.04 | 0.05 | 0.08 | 0.06,tr | 0.13 | 0.10 | 99.57 | 0.39 | 062083 |

| Timepoint/ Condition | Appearance and Particulates (SAP009) | A/N |
|---|---|---|
| Initial | Clear colourless solution with some fibres but no particulates believed to be drug-related. | 062083 |

LIQUID FORMULATIONS OF COMPOUNDS ACTIVE AT SULFONYLUREA RECEPTORS

The present application is a continuation of U.S. patent application Ser. No. 12/863,525, filed on Oct. 12, 2010, which is a U.S. National Stage Application under 35 U.S.C. 371 of PCT/US2009/032455, filed on Jan. 29, 2009, which claims priority to U.S. Provisional Application No. 61/024,499, filed Jan. 29, 2008, each of which is incorporated herein by reference in its entirety

FIELD OF THE INVENTION

The present invention provides liquid formulations of compounds active at sulfonylurea receptors and suitable for administration to a patient in need of treatment with such compounds, methods for using the novel formulations, and kits providing the formulations for clinical use.

BACKGROUND OF THE INVENTION

Macromolecules termed "sulfonylurea receptors" (SUR) are found in many body tissues and are important in many physiological activities. Among many important functions, SUR are involved in insulin release from pancreatic beta cells, and may affect blood pressure by affecting vascular smooth muscle. There are multiple SUR, including a type 1 sulfonylurea receptor (SURD, a type 2 sulfonylurea receptor (SUR2) and subtypes of these receptors. Molecularly distinct SURs are coupled to distinct ion channel moieties in various tissues to form, for example, different $K_{ATP}$ channels with distinguishable physiological and pharmacological characteristics. $K_{ATP}$ channels in pancreatic beta cells are formed from SUR1 linked with a $K^+$ channel, whereas the cardiac and smooth muscle $K_{ATP}$ channels are formed from SUR2A and SUR2B, respectively, linked to $K^+$ channels.

A newly identified calcium and adenosine triphosphate sensitive non-selective cation channel ($NC_{ca-ATP}$ channel) is another ion channel affected by compounds that affect SUR. $NC_{ca-ATP}$ channels are found in neural tissue and neural cells following trauma, stroke, ischemia, and other injuries and conditions (Simard et al., U.S. patent application Ser. No. 10/391,561, published as 2003/0215889; Simard et al., U.S. patent application Ser. No. 10/391,561, published as 2006/00100183).

Sulfonylurea drugs are commonly used to treat patients having blood glucose level disorders, such as patients with diabetes. Sulfonylurea drugs have other uses in addition to treating diabetes. For example, sulfonylurea drugs interact with SUR and affect the activity of ion channels found in many tissues, including neural tissue such as neurons, glial cells, and other cells in the brain, spinal cord, and peripheral nervous system. Ion channel types associated with SUR and affected by sulfonylurea (and other drugs acting on SUR) include potassium channels and non-selective channels. SUR is responsible for activation of some potassium channels by a chemically diverse group of agents termed $K^+$ channel openers, such as diazoxide, pinacidil, and cromakalin.

Sulfonylurea drugs commonly used in clinical applications include antidiabetic sulfonylureas such as glibenclamide and tolbutamide, and may also include repaglinide, nateglinide, meglitinide, midaglizole, LY397364, LY389382, glyclazide, glimepiride and other drugs or metabolites of drugs which interact with SUR.

Such drugs are typically poorly water soluble, and are commonly given as pills or in other solid form. However, some patients are not able to swallow pills, or otherwise would be better served if these drugs were readily available for delivery in another form besides solid pills or powders. Oral administration of solid dosage forms typically results in a time-lag before clinically effective dose levels are reached in the patient's tissues and internal fluids, and makes maintenance of constant levels of drug in those tissues and fluids difficult. Furthermore, pH fluctuations in the stomach or gut can alter the absorption rates of drugs. Accordingly, there is need in the art for alternative formulations of drugs acting at a SUR, including alternative formulations of sulfonylurea drugs such as glibenclamide, tolbutamide, and other drugs that act on SUR.

SUMMARY OF THE INVENTION

New and useful liquid formulations of compounds that act at a SUR are disclosed herein. Such liquid formulations are suitable for intravenous, intra-arterial, intrathecal, parenteral, intraperitoneal, intracerebroventricular, subcutaneous, oral, buccal, sublingual, intracavernous, and topical, or other routes of administration. The liquid formulations having features of the invention may be administered to patients in need of treatment with drugs that act at a SUR according to novel methods disclosed herein. Kits including the novel liquid formulations and instructions for their use according to the novel methods of the invention are also provided.

A liquid formulation suitable for administration to a patient and having features of the invention may include: a compound which interacts with a sulfonylurea receptor (SUR), water, a solvent, and a co-solvent. In embodiments, a liquid formulation suitable for administration to a patient and having features of the invention may include a compound which interacts with a SUR, water, a solvent, a co-solvent, and a surfactant. Liquid formulations having features of the invention may also include one or more of pharmaceutically acceptable ingredients, including, for example, buffers, osmoticants, preservatives, antioxidants, excipients, and other pharmaceutically acceptable ingredients.

In embodiments of the liquid formulations having features of the invention, the compound which interacts with a SUR is a compound that interacts with a Type 1 sulfonylurea receptor (SURD, and may be a sulfonylurea compound, such as an antidiabetic sulfonylurea compound. In preferred embodiments, the compound may be glibenclamide or tolbutamide.

Accordingly, disclosed herein are solutions and methods providing liquid formulations including a compound or compounds that act at a SUR (SUR-active compound or compounds). Liquid formulations having features of the invention include a SUR-active compound or compounds at a concentration of greater than about 0.04 mg/ml, a solvent, and optionally include a surfactant. A liquid formulation having features of the invention may further include one or more of a co-solvent and a pH buffer. Provided herein are also liquid formulations comprising dilutions of the liquid formulations disclosed above to provide formulations including water, wherein the SUR-active compound remains dissolved in the liquid formulation following dilution. In preferred embodiments, the liquid formulations disclosed above are diluted with a diluent suitable for administration to a patient, and wherein the diluent is a water-based solution including one or more of a salt, a sugar, a sugar alcohol, and a pH buffer. Liquid formulations having features of the invention may also include further ingredients such as, for example, preservatives and antioxidants, and other ingredients customarily included in clinical formulations. The liquid formulations may be administered undiluted or slightly diluted as a bolus, by syringe pump or injection, and may also be more extensively diluted and administered as an infusion, including administration by an infusion pump or syringe pump.

Provided herein are multiple embodiments of liquid formulations of SUR-active compounds, including a) concentrated embodiments with concentrations greater than about 0.04 mg/ml (suitable, for example, for bolus administration or for injection by infusion pump or syringe pump); b) concentrated embodiments suitable for dilution with pharmaceutically acceptable diluents, which diluents are typically water-based solutions including salts and/or sugars and/or sugar alcohols (also suitable, for example, for bolus administration or for injection by infusion pump or syringe pump); c) diluted embodiments, with solutions which may have lower concentrations of SUR-active compounds, which may include pharmaceutically acceptable diluents, which diluents are typically water-based solutions including salts and/or sugars and/or sugar alcohols (suitable for infusion or injection, as a bolus or for administration over an extended period of time); and other embodiments. In embodiments of the liquid formulations suitable for bolus administration to a patient, or for storage before use, the liquid formulations may have a concentration of SUR-active compound or compounds of greater than about 0.04 mg/ml, or greater than about 0.1 mg/ml, or greater than about 1 mg/ml, or greater than about 10 mg/ml, or greater than about 20 mg/ml or other amounts. In further embodiments, liquid formulations having features of the invention are diluted liquid formulations having a concentration of a SUR-active compound suitable for administration to a patient over an extended period of time, where the compound active at a SUR does not precipitate from solution during or following dilution, or when frozen or refrigerated.

The liquid formulations disclosed herein are useful for administration of SUR-active compounds to patients in need of such compounds. For example, administration of the liquid formulations containing SUR-active compounds may be useful in alleviating, reducing, or preventing brain swelling, neural cell swelling, or other damage to a patient's nervous system that may result from, or occur incidental to, stroke, head trauma, spinal cord injury, cardiac arrest leading to an interruption of blood flow to the brain, or other condition.

For example, glibenclamide is commonly used to treat certain forms of diabetes, and as such is administered orally. However, the present inventors have found that glibenclamide may be used as a treatment for stroke. Use of glibenclamide in the treatment of stroke may require an intravenous formulation, and therefore formulation experiments have focused on the development of a suitable injectable formulation of glibenclamide at various concentrations (e.g., at 1 mg/ml). For example, glibenclamide for injection may be administered as a bolus for the initial treatment (4 mg), and then diluted for a continuous 5-7 day infusion at 20 mg/day. Adequate solubility of glibenclamide is achieved in some embodiments, for example, by formulating with polyethylene glycol 300 (PEG 300) and ethanol (which are both better solvents for glibenclamide than water alone) together with maintaining a high pH, such as, e.g., a pH above pH 8, or preferably above pH 9, or higher.

Liquid formulations disclosed herein may be used for bolus injection into the vasculature (e.g., intravenous or intra-arterial administration), or cerebrospinal fluid, or other destination of administration, of a patient-suffering from stroke, head trauma, spinal cord injury, cardiac arrest leading to an interruption of blood flow to the brain, or other condition in which the sufferer is at risk of brain swelling or neural cell swelling. Liquid formulations disclosed herein may be used for infusion, such as infusion over an extended period of time, into the vasculature, cerebrospinal fluid, or other destination of administration, of a patient suffering from stroke, head trauma, spinal cord injury, cardiac arrest leading to an interruption of blood flow to the brain, or other condition in which the sufferer is at risk of brain swelling or neural cell swelling. In a yet further example, the liquid formulations disclosed herein may be used for intracerebroventricular or intrathecal administration to a patient suffering from stroke, head trauma, spinal cord injury, cardiac arrest leading to an interruption of blood flow to the brain, or other condition in which the sufferer is at risk of brain swelling or neural cell swelling. The liquid formulations disclosed herein may further be useful for parenteral, intraperitoneal, subcutaneous, oral, buccal, sublingual, intracavernous, and topical, or other administration to a patient in need of a SUR-active compound.

Accordingly, it will be understood that disclosed herein are also methods for administering a SUR-active compound to a patient in need of treatment with a SUR-active compound. For example, provided herein are methods of treating a patient suffering from stroke, head trauma, spinal cord injury, cardiac arrest leading to an interruption of blood flow to the brain, or other condition in which the sufferer is at risk of brain swelling or neural cell swelling comprising administration of an effective dose of a SUR-active compound provided via a liquid formulation of a SUR-active compound having features of the invention. Methods of treating a patient in need of administration of a SUR-active compound include intravenous, intra-arterial, intrathecal, parenteral, intraperitoneal, intracerebroventricular, subcutaneous, oral, buccal, sublingual, intracavernous, and topical, or other routes of administration. Administration of SUR-active compounds via liquid formulation, and in particular via intra-arterial or intravenous administration, provides rapid and readily controlled increase in circulating drug concentrations, providing rapid onset of treatment which allows rapid adjustment and ready maintenance of circulating drug concentrations.

The liquid formulations and methods of using the liquid formulations provide alternative forms of administration of SUR-active compounds, aid in such administration by improved ease of administration, and allow ready administration to patients in need thereof who may not be able to swallow solid dosage forms or who may be in need of rapid pharmacological availability of the drug without the lag-time often encountered with administration of drugs by solid, oral dosage forms.

These and other advantages of the invention will become more apparent from the following detailed description of the liquid formulations, compositions, methods and kits having features of the invention.

BRIEF DESCRIPTION OF THE DRAWINGS

FIG. 3 shows glibenclamide stability in various formulations. FIG. 3A shows glibenclamide stability at a concentration of 1 mg/ml at pH 9, with 5 mM meglumine, when stored at 2-8° C. FIG. 3B shows glibenclamide stability at a concentration of 1 mg/ml at pH 9, with 5 mM meglumine, when stored at 25° C. and 60% relative humidity. FIG. 3C shows glibenclamide stability at a concentration of 1 mg/ml at pH 9, with 5 mM meglumine, when stored at 40° C. and 75% relative humidity. FIG. 3D shows glibenclamide stability at a concentration of 1 mg/ml at pH 9, with 5 mM diethanolamine, when stored at 2-8° C. FIG. 3E shows glibenclamide stability at a concentration of 1 mg/ml at pH 9, with 5 mM diethanolamine, when stored at 25° C. and 60% relative humidity. FIG. 3F shows glibenclamide stability at a concentration of 1 mg/ml at pH 9, with 5 mM diethanolamine, when stored at 40° C. and 75% relative humidity. FIG. 3G shows glibenclamide stability at a concentration of 1 mg/ml at pH 9.5, with 10 mM meglumine, when stored at 2-8° C. FIG. 3H shows glibenclamide stability at a concentration of 1 mg/ml at pH 9.5, with 10 mM meglumine, when stored at 25° C. and 60% relative humidity. FIG. 3I shows glibenclamide stability at a concentration of 1 mg/ml at pH 9.5, with 10 mM meglumine, when stored at 40° C. and 75% relative humidity. FIG. 3 J shows glibenclamide stability at a concentration of 1 mg/ml in a non-aqueous formulation, when stored at 25° C. and 60% relative humidity.

DETAILED DESCRIPTION OF THE INVENTION

Definitions

Figure 1:
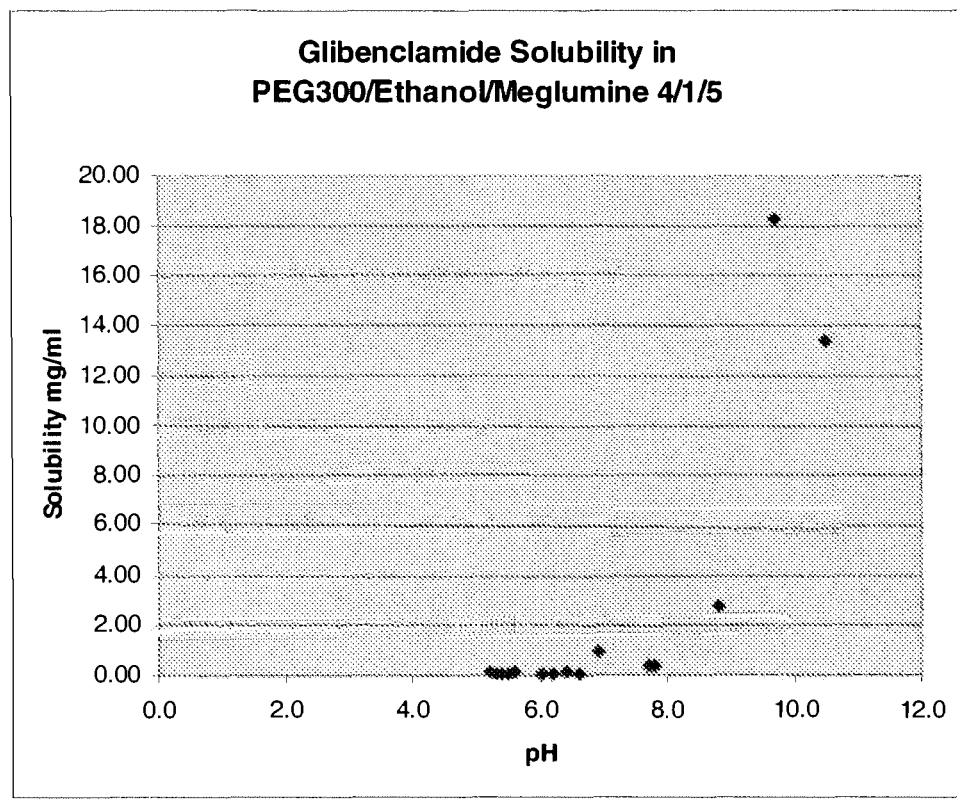
FIG. 1 shows glibenclamide solubility at different pH values in a solution including polyethylene glycol, ethanol, and meglumine.

The phrase "SUR-active compound" and similar phrases, such as "a compound which is pharmaceutically active at a sulfonylurea receptor" as used herein refer to pharmaceutically acceptable compounds that act at a SUR. SUR-active compounds include compounds active at SUR1, at SUR2, or at both SUR1 and SUR2 type SUR, and include both sulfonylurea compounds and non-sulfonylurea compounds. SUR-active compounds suitable for use in the practice of the invention include antidiabetic sulfonylureas such as glibenclamide and tolbutamide, and may also include repaglinide, nateglinide, meglitinide, midaglizole, LY397364, LY389382, glyclazide, glimepiride and other drugs or metabolites of drugs which interact with SUR. In some preferred embodiments of a liquid formulation having features of the invention, the SUR-active compound is selected from glibenclamide and tolbutamide. In further preferred embodiments, the compound is glibenclamide. In some embodiments, a liquid formulation having features of the invention includes more than one SUR-active compound, and in embodiments may include several SUR-active compounds.

As used herein, the term "pharmaceutical composition" refers to a mixture including one or more SUR-active compounds, or pharmaceutically acceptable salts thereof, with other chemical components, such as pharmaceutically acceptable solvents, co-solvents, surfactants, buffers, carriers and/or excipients. The purpose of a pharmaceutical composition is to facilitate administration of a compound to an organism.

As used herein, the term "pharmaceutically acceptable" refers to solvents, co-solvents, surfactants, carriers, diluents, excipients, buffers, salts, and/or other components that are compatible with the other ingredients of the formulation and are not deleterious to the recipient thereof. Thus, pharmaceutically acceptable components of a formulation, pharmaceutical composition, or mixture, are those components that do not prevent the therapeutic compound from exerting a therapeutic effect which are suitable for clinical use without excessive toxicity, irritation, allergic response, or other problem or complication, according to accepted medical belief and practice.

Examples of pharmaceutically acceptable reagents are provided in The United States Pharmacopeia, The National Formulary, adopted at the United States Pharmacopeial Convention, held in Rockville, Md. in 1990 and FDA Inactive Ingredient Guide 1990, 1996 issued by the U.S. Food and Drug Administration (which references are hereby incorporated herein by reference in their entireties).

A pharmaceutically acceptable infusion solution includes water.

The term "pharmaceutically acceptable alcohol" as used herein refers to alcohols, which are liquids at about room temperature (approximately 20° C.). Pharmaceutically acceptable alcohols include ethanol, benzyl alcohol, propylene glycol, 2-(2-ethoxyethoxy)ethanol (TRANSCUTOL, Gattefosse, Westwood, N.J. 07675), glycerol, and combinations or mixtures thereof.

As used herein, the term "solvent" refers to a compound into which a SUR-active compound may dissolve. As SUR-active compounds are typically hydrophobic, solvents suitable for the practice of the invention include hydrophobic solvents such as organic solvents. Water-soluble organic solvents suitable for use in pharmaceutically acceptable formulations having features of the invention include: polyethylene glycol 300, polyethylene glycol 400, ethanol, propylene glycol, glycerin, N-methyl-2-pyrrolidone, dimethylacetamide, and dimethylsulfoxide). A discussion and listing of such solvents may be found, for example, in Strickley, *Pharmaceutical Research* 21(2):201-230 (2004), the contents of which are hereby incorporated by reference.

As used herein, the term "co-solvent" is used to refer to a material which is not necessarily an acceptable solvent that is added to a generally small amount of active solvent to form a mixture which has enhanced solvent power. For example, co-solvents suitable for use in liquid formulations having features of the invention include propylene glycol, polyalkylene glycols, cyclodextrins (such as, e.g., sulfobutylether β-cyclodextrin and hydroxypropyl β-cyclodextrin), chitosan, and N-methyl-2-pyrrolidone (Pharmasolve®).

As used herein, the term "polyalkylene glycol" refers to a polyethylene glycol, polypropylene glycol or polybutylene glycol having a molecular weight of less than about 5000, terminating in either a hydroxy or alkyl ether moiety.

As used herein, the term "surfactant" refers to a compound or molecule effective to increase the water solubility of a hydrophobic compound. A surfactant is typically an amphipathic molecule having both hydrophobic and hydrophilic properties. Further, the term "surfactant" as used herein in reference to liquid formulations of SUR-active compounds includes pharmaceutically acceptable non-ionic surfactants. In some preferred embodiments of the liquid formulations disclose herein, the surfactant is a pharmaceutically acceptable non-ionic surfactant. Preferred pharmaceutically acceptable non-ionic surfactants include polyoxyethylenepolypropylene glycols (e.g., POLOXAMER 68 (BASF Corp.) or a mono fatty acid ester of polyoxyethylene (20) sorbitan monooleate (TWEEN 80), polyoxyethylene (20) sorbitan monostearate (TWEEN 60), polyoxyethylene (20) sorbitan monopalmitate (TWEEN 40), polyoxyethylene (20) sorbitan monolaurate (TWEEN 20), POLYSORBATE 80 (Spectrum Chemical Mfg. Corp.) and other polyoxyethylene sorbitan fatty acid esters, glyceryl monooleate, polyvinyl alcohol, ethylene oxide copolymers such as PLURONIC (a polyether; BASF Corp.) and TETRONIC (BASF Corp.), polyol moieties, and sorbitan esters. Suitable surfactants further include polyoxyethylene castor oil derivatives (e.g., polyoxyethyleneglyceroltriricinoleate or polyoxyl 35 castor oil (CREMOPHOR EL, BASF Corp.), polyoxyethyleneglycerol oxystearate (CREMOPHOR RH 40 (polyethyleneglycol 40 hydrogenated castor oil) or CREMOPHOR RH 60 (polyethyleneglycol 60 hydrogenated castor oil), BASF Corp.) and the like)).

Non-ionic surfactants suitable for use in pharmaceutically acceptable formulations may include: Cremophor EL, Cremophor RH 40, Cremophor RH 60, d-tocopherol polyethylene glycol 1000 succinate, polysorbate 20, polysorbate 80, Solutol HS 15, sorbitan monooleate, poloxarner 407, Labrafil M-1944CS, Labrafil M-2125CS, Labrasol, Gelucire 44/14, Softigen 767, and mono- and di-fatty acid esters of PEG 300, 400, or 1750). (Strickley, *Pharmaceutical Research* 21(2):201-230 (2004)).

In some preferred embodiments, surfactants such as TWEEN 80, POLYSORBATE 80 or ethoxylated castor oils, such as CREMOPHOR EL (BASF Corp.) are used for the formulation.

Surfactants suitable for use in liquid formulations having features of the invention include polyoxyethylene sorbitan fatty acid esters, glyceryl monooleate, polyvinyl alcohol, ethylene oxide copolymers, polyol moieties, sorbitan esters, and ethoxylated castor oils; in a preferred embodiment polyoxyethylene sorbitan fatty acid ester includes POLYSORBATE 80 and ethoxylated castor oil includes polyoxyl 35 castor oil.

As used herein, a buffer is a compound or complex that is effective to maintain the pH of a water solution containing the buffer within a desired range of pH values. In preferred embodiments, a buffer is a pharmacologically acceptable buffer. Suitable buffers include lactate, acetate, citrate, phosphate, carbonate, tromethamine, glutamate, glycine, succinate, meglumine and diethanolamine buffers.

Pharmaceutically acceptable acids or bases are included in the formulation to adjust the pH to obtain desirable solubility or stability. Examples include inorganic or organic acids such as methanesulfonic acid, lactic acid, tartaric acid, citric acid, succinic acid, hydrochloric acid, hydrobromic acid, sulfuric acid, nitric acid, phosphoric acid, ethanesulfonic acid, p-toluenesulfonic acid, salicylic acid and the like, or inorganic or organic bases such as sodium hydroxide, potassium hydroxide, ammonium hydroxide, calcium hydroxide, choline, n-methyl glucamine, diethylamine, procaine and the like. Preferably, organic acids such as methane sulfonic acid or lactic acid and bases such as sodium hydroxide are used.

As used herein, the term "diluent" refers to a water-based liquid useful for mixing with a first liquid formulation having features of the invention to provide a second liquid formulation having features of the invention that has a lower concentration of SUR-active compound than the first liquid formulation. Diluents include water, water containing a salt (e.g., a saline solution), water containing a sugar, water containing a sugar alcohol, water containing a buffer, and combinations thereof.

The term "pharmaceutically acceptable diluent" refers to a non-toxic diluent that does not adversely modify the biological activity of the compounds of the preferred embodiments of the present invention. The added amount of a pharmaceutically acceptable diluent should be sufficient to avoid hemolysis. Examples of suitable pharmaceutically acceptable diluents such as WFI (water for injection) and solutions containing isotonic saline are known in the art. Pharmaceutically acceptable aqueous solutions include 0.9% saline, 0.45% N saline, WFI (water for injection), D5W (5% dextrose in water), and a dextrose/saline solution (D2.5W (i.e., 2.5% dextrose in water) and 0.45% N saline). Alternatively, the "pharmaceutically acceptable diluent" includes buffer solutions to maintain the pH of the formulation between 2.5 to 10.5. These buffers may be composed of lactates, acetates, citrates, phosphates, carbonates, tromethamine, glutamates, glycine and others known in art. Preferably, diluents such as 0.9% saline or lactate, phosphate or tromethamine buffers are used.

As used herein, pharmaceutically acceptable saline solution is a solution suitable for administration to a patient that includes water and sodium chloride, and may optionally contain buffers, preservatives, or other components, typically in small amounts. For example, pharmaceutically acceptable saline solutions include 0.9% saline (9 g NaCl in 100 ml distilled, filtered water, containing 150 mM sodium and 150 mM chloride) and saline solutions having 154 mM sodium and 154 mM chloride.

As used herein, "Ringer's solution" refers to a pharmaceutically acceptable buffered saline solution having sodium chloride, potassium chloride, and calcium chloride salts.

As used herein, "Hartmann's solution" refers to a lactate Ringer's solution. A typical Hartmann's solution includes 131 mM sodium, 5 mM potassium, 2 mM calcium, 11 mM chloride, and 29 mM lactate (sodium chloride 0.6%, sodium lactate 0.25%, potassium chloride 0.04%, calcium chloride 0.027%).

As used herein, the term "sugar" refers to any sugar, including monosaccharides, di-saccharides, and polysaccharides. Sugars suitable for use in the liquid formulations disclosed herein include monosaccharides such as glucose, fructose, mannose, galactose, arabinose, xylose and ribose, etc., and also oligosaccharides such as disaccharides (maltose, lactose, sucrose, trehalose, etc.) and trisaccharides (e.g. raffinose, maltotriose, etc.).

As used herein, the term "sugar alcohol" refers to any sugar, including monosaccharides, di-saccharides, and polysaccharides, having a hydroxyl moiety. Pharmaceutically acceptable sugars and sugar alcohols include mannitol, sorbitol, glycerol, xylitol, dulcitol, arabitol, and others, including alcohols of those sugars previously named herein.

As used herein, the term "pharmaceutically acceptable osmolarity" refers to an osmolarity near to, or the same as, a normal body fluid, such as normal blood plasma. Thus, a pharmaceutically acceptable osmolarity may be an osmolarity of between about 250 milliOsmoles/liter (mOsm) and about 350 mOsm; or between about 280 mOsm and about 320 mOsm; or between about 290 mOsm and about 310 mOsm.

The term "antioxidant" includes various substances capable of protecting the parent molecule from oxidization and includes sodium metabisulfite, sodium bisulfite, sodium sulfite, cysteine, methionine, ascorbic acid, BHA (butylated hydroxyanisole), BHT (butylated hydroxytoluene), vitamin E (tocoferols), vitamin E PEG 1000 succinate and the like. Preferred antioxidants include sodium metabisulfite, sodium bisulfite, sodium sulfite, cysteine and methionine, or mixtures thereof. The types of oxidation that are prevented by the antioxidant are, without limitation, the oxidation of alkyl or aryl groups on the parent molecule.

It will be understood that cited values are to be taken to indicate the values cited and also to denote a range of suitable values, within about 50% above and about 50% below the stated value. For example, if where a formulation is noted as including a constituent, such as 20% PEG, it will be understood that suitable formulations may include between about 10%-30% PEG, with concomitant adjustment of other values as necessary.

Liquid Formulations

Liquid formulations of SUR-active compounds, and methods and kits for using the liquid formulations are disclosed herein. The liquid formulations are suitable for administration of SUR-active compounds to patients in need of treatment using such compounds. Liquid formulations having features of the invention include a SUR-active compound, a solvent, a co-solvent, optionally a surfactant, optionally a buffer, and may include other pharmaceutically acceptable ingredients.

Compounds that act at a SUR and are suitable for the practice of the invention are termed herein "SUR-active compounds" and may be sulfonylurea compounds, and may be non-sulfonylurea compounds that act at a SUR. SUR-active compounds suitable for use in the practice of the invention include antidiabetic sulfonylureas such as glibenclamide and tolbutamide, and may also include repaglinide, nateglinide, meglitinide, midaglizole, LY397364, LY389382, glyclazide, glimepiride and other drugs or metabolites of drugs which interact with SUR. In some preferred embodiments of a liquid formulation having features of the invention, the SUR-active compound is selected from glibenclamide and tolbutamide. In further preferred embodiments, the compound is glibenclamide. In some embodiments, a liquid formulation having features of the invention includes more than one SUR-active compound, and in embodiments may include several SUR-active compounds.

The solvent may be a solvent suitable for solubilizing a hydrophobic molecule and for aiding in dissolving a hydrophobic molecule into a water solution. For example, the solvent may be an alcohol, such as ethanol, or a sulfoxide compound, such as dimethyl sulfoxide (DMSO), or an acetamide, such as dimethylacetamide, and other solvents, such as tetraglycol (also known as glycofurol or Tetrahydrofurfuryl Alcohol Polyethyleneglycol Ether), and dimethylacetamide (DMA). Although all the named solvents are suitable, the inventors have discovered that ethanol, tetraglycol and DMA are preferred solvents for the liquid formulations having features of the invention.

The co-solvent may be suitable for solubilizing a hydrophobic molecule, where the co-solvent is compatible with a solvent useful for dissolving a compound into a water solution. A co-solvent may be, for example, propylene glycol, a polyalkylene glycol, glycerin, N-methyl-2-pyrrolidone, a cyclodextrin, or other molecule suitable for dissolving a hydrophobic drug compound and aiding its further dissolution into a water solution. The inventors have discovered that polyalkylene glycols, polyethylene glycol in particular, are to be preferred over propylene glycol as co-solvents. Preferred polyethylene glycols include PEG 300 and PEG 400.

A surfactant may be, for example, a non-ionic surfactant, or any pharmaceutically acceptable surfactant. In embodiments, one or more compounds may find use in one or more of the named categories. For example, a component of a liquid formulation having features of the invention may act as both a co-solvent and as a surfactant (e.g., a Crernophor®, d-α-tocopherol-polyethylene glycol 1000 succinate, and others). The liquid formulation may include an anti-oxidant. Suitable anti-oxidants include, for example, ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g., stabilising agents. The concentration of an anti-oxidant and/or a stabilizing agent in the composition may be, for example, from about 0.1% w/w to about 5% w/w.

Concentrated solutions containing a SUR-active compound having features of the invention may have a pH of about pH 7 to about pH 12, or about pH 7.4 to about pH 11.5, or other pH range within the range of about pH 7 to about pH 12. The inventors have determined that a concentrated solution of SUR-active compound having a pH of about pH 9 to about pH 11, including a pH of about 9 (e.g., about pH 8.5 to about pH 9.5) or a pH of about 10 (e.g., about pH 9.5 to about pH 10.5) is suitable for use for bolus injections of SUR-active compound, and is also suitable for dilution, with a pharmaceutically acceptable solution such as Hartmann's solution, for administration of lower concentrations of SUR-active compounds. For example, a concentrated solution having a SUR-active compound concentration of 1 mg/ml at a pH of about 9.5 could be diluted 1:50 in Hartmann's solution to provide an infusion solution for delivery of a SUR-active compound at a concentration of about 0.02 mg/ml in Hartmann's at an acceptable pH.

The inventors have determined that a concentrated solution of SUR-active compound having a pH of about 8 (e.g., about pH 7.5 to about pH 8.5) is suitable for use for bolus injections of SUR-active compound, and is also suitable for dilution 1:1 or 1:2, with a pharmaceutically acceptable solution such as 0.9% NaCl, for administration of lower concentrations of SUR-active compounds. For example, a concentrated solution having a SUR-active compound concentration of 1 mg/ml at a pH of about 8.4 could be diluted 1:1 in 0.9% NaCl solution to provide an infusion solution for delivery of a SUR-active compound at a concentration of about 0.5 mg/ml in Hartmann's at a pharmaceutically acceptable pH.

Liquid formulations having features of the invention include liquid formulations having a SUR-active compound solubilized at a pH suitable for bolus infusion into a patient. A pH of a liquid formulation suitable for bolus infusion into a patient may be a pH of no more than about pH 11.5, or may be a pH of no more than about pH 9.5, or may be a pH of no more than about pH 9, or may be a pH of no more than about pH 8.5, or may be a pH of no more than about pH 8, or may be a pH of no more than about pH 7.4. In embodiments, a pH of a liquid formulation suitable for bolus infusion into a patient may be a pH of between about pH 8.5 and about pH 9.5, or may be a pH of between about pH 8 and about pH 9. In embodiments, the pH of a liquid formulation suitable for bolus infusion into a patient may be a pH of between about pH 7.4 and about pH 9.5, or may be a pH of between about pH 7.4 and about pH 8.5.

Liquid formulations having features of the invention may further include a pharmaceutically acceptable buffer. In embodiments, a liquid formulation having features of the invention includes more than one pharmaceutically acceptable buffer. Pharmaceutically acceptable buffers suitable for use in liquid formulations having features of the invention include bicarbonate buffers, phosphate buffers, lactate buffers, and other buffers. In embodiments of the liquid formulations having features of the invention, the buffer or buffers may aid in maintaining the pH at a desired level.

Figure 2:
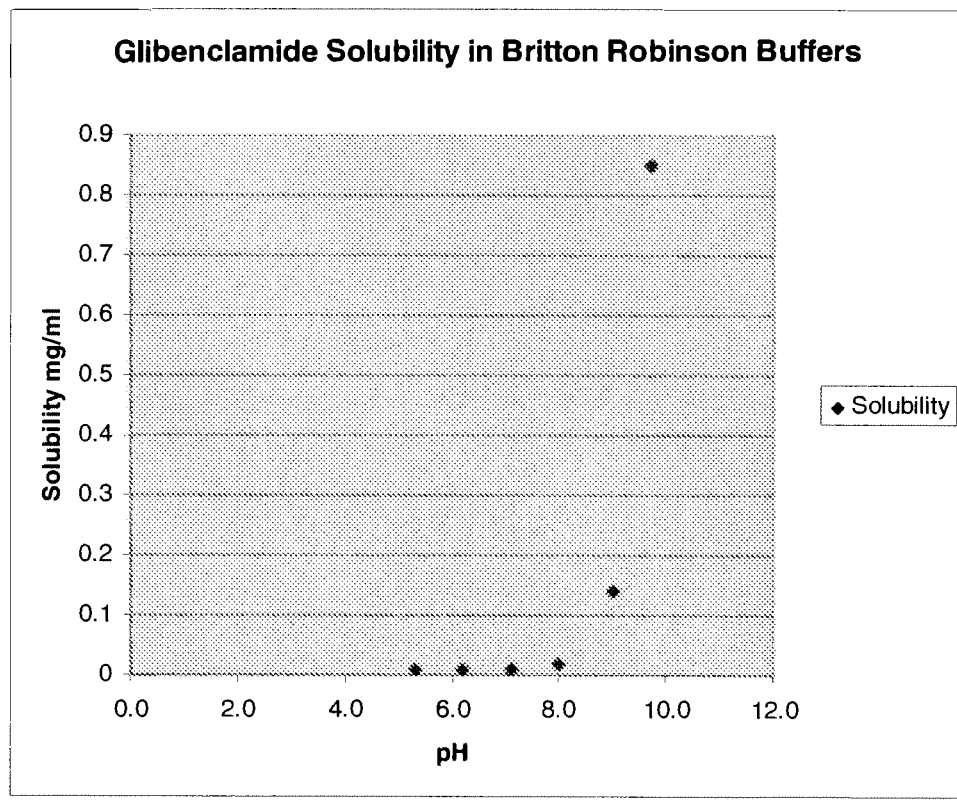
FIG. 2 shows glibenclamide solubility in a Britton Robinson buffer solution at different pH values.

SUR-active compounds, such as glibenclamide and tolbutamide, are reported to be sparingly soluble in water, being soluble in concentrations of less than about 0.04 mg/ml. In order to develop liquid formulations of SUR-active compounds able to contain greater than about 0.05 mg/ml in water-based solutions, the solubility of SUR-active compounds at different values of pH was investigated. As shown in FIG. 1, glibenclamide solubility was measured in solutions containing 40% PEG 300, 10% ethanol, and 50% water with a meglumine buffer adjusting the pH to the several indicated values. The solubility of glibenclamide was greatly increased at basic pH values, such as at pH values greater than about pH 8. As shown in FIG. 2, similar results were also obtained with measurements of glibenclamide solubility made in Britton Robinson buffers (water solutions including phosphoric acid, acetic acid and boric acid). It was observed that the solubility in Meglumine at pH 10 was much better than had been seen with a previously examined pH 10 buffer. These differences may reflect the pH differences between the buffers (Meglumine has a pH of 10.1 whereas the Britton Robinson "pH 10" buffer has a pH of 9.7). As illustrated in FIG. 1, slight changes of pH in this pH region result in large changes in observed solubility. Solubility at high pH levels was increased as pH was further increased: the solubility of glibenclamide in the Britton Robinson buffer at pH 9.0 was 0.14 mg/ml, while glibenclamide solubility in the Britton Robinson buffer at pH 9.7 was increased to 0.86 mg/ml. Similarly, glibenclamide solubility in Meglumine at pH 10.1 was 2.35 mg/ml, while increasing pH (with Meglumine buffer) to pH 10.7 increased glibenclamide solubility to 8.12 mg/ml.

Thus, the inventors have demonstrated that SUR-active compounds such as glibenclamide may be dissolved in water based solutions at concentrations greater than about 0.04 mg/ml at pH levels of about pH 8 or greater. The inventors thus disclose herein that liquid formulations having relatively high concentrations (greater than about 0.05 mg/ml) of SUR-active compounds such as glibenclamide preferably have relatively high pH values, such as above about pH 8, or above about pH 8.5, or above about pH 9, for example. Such formulations do not precipitate active components from solution during or following dilution, or when frozen or refrigerated (e.g., to improve shelf life and/or reduce hydrolysis).

The inventors have further discovered that water-based solutions containing relatively high concentrations of SUR-active compounds may be diluted with water-based solutions to more dilute concentrations, and to lower pH levels, without precipitation of the SUR-active compound. Such dilutions, and such lowering of pH levels without precipitation of the SUR-active compounds is made possible by the liquid formulations disclosed herein, in which the pH of the solution drops slowly with dilution. Inclusion of a buffer, such as meglumine, diethanolamine, or other buffer, aids in providing solutions suitable for dilution and reduction of pH from relatively high values (e.g., greater than about pH 8 or more) to more physiologically acceptable pH values (e.g., about pH 8 or less than about pH 8).

Liquid formulations having features of the invention suitable for bolus infusion into a patient may also be suitable for dilution with a pharmaceutically acceptable diluent effective to provide a diluted liquid formulation in which the SUR-active compound remains solubilized following the dilution. A liquid formulation having features of the invention that provides a diluted liquid formulation in which the SUR-active compound remains solubilized may include a buffer. In embodiments of the liquid formulations having features of the invention, the buffer or buffers may aid in providing a desired pH after dilution of the solution to a more dilute concentration of the SUR-active compound or SUR-active compounds.

Such diluted solutions may have a pH suitable for infusion into a patient for an extended period of time. A pH of a diluted solution having features of the invention, and suitable for infusion into a patient for an extended period of time may be a pH of no more than about pH 8.5, or may be a pH of no more than about pH 8, or may be a pH of no more than about pH 7.5, or may be a pH of about pH 7. In embodiments, a pH of a diluted liquid formulation suitable for infusion into a patient for an extended period of time may be a pH of between about pH 7.5 and about pH 8.5, or may be a pH of between about pH 7 and about pH 8.

A liquid formulation for administration to a patient having features of the invention, comprising a dilution of the liquid formulation having a concentration of a SUR-active compound of greater than about 0.05 mg/ml, may include, as a diluent, a pharmaceutically acceptable water-based solution. A pharmaceutically acceptable water-based solution may be any solution which is suitable for infusion or injection into a patient. Such a pharmaceutically acceptable water-based solution may be a saline solution or other pharmaceutically acceptable salt solution; a glucose solution; a solution containing a sugar (which may be, e.g., a monosaccharide or a polysaccharide); a solution including a sugar alcohol; a solution including a salt and a sugar; a solution including a salt and a sugar alcohol, a Ringer's solution, a lactate Ringer's solution (Hartmann's solution), or other pharmaceutically acceptable solution. Such a pharmaceutically acceptable water-based solution may be a buffered solution effective to maintain solution pH at a desired level or within a desired pH range.

The desired solubility of a SUR-active compound may be achieved through a combination of inclusion of excipients and of pH adjustment. For example, the desired solubility of glibenclamide may be achieved through a combination of inclusion in the solution of excipients and of pH adjustment. The pH adjustment may include inclusion or addition of a buffer, or buffers, in the solution. For example, the solution including a SUR-active compound may include a pH buffer. In a further example, a water-based diluent solution, that may be added to the solution, including a SUR-active compound, may include a pH buffer. In a further example, the solution including a SUR-active compound and the water-based solution to be added may each include a buffer or buffers effective to control the pH of the solution to a desired degree. The solutions that are mixed together to provide a diluted liquid formulation having features of the invention may be configured so that the pH is buffered in order to achieve the desired dilution without precipitation of the SUR-active compound.

A pharmaceutically acceptable diluent may have an osmolarity near to, or the same as, a normal body fluid, such as normal blood plasma. In embodiments, a pharmaceutically acceptable diluent may have an osmolarity adjusted so that the osmolarity of the diluted solution, after addition of the diluent, is near to, or the same as, the osmolarity of a normal body fluid, such as normal blood plasma.

A liquid formulation having features of the invention may have an osmolarity that is physiologically tolerable by a patient. Thus, although it will be understood that a liquid formulation for bolus infusion need not have a pharmaceutically acceptable osmolarity, in embodiments a liquid formulation for bolus infusion may have a pharmaceutically acceptable osmolarity. Similarly, a diluted liquid formulation for infusion over an extended period of time may have a pharmaceutically acceptable osmolarity.

For example, a diluted liquid formulation having features of the invention may have an osmolarity that is physiologically tolerable by a patient for an infusion lasting greater than about 3 hours, or greater than about 6 hours. A diluted liquid formulation having features of the invention may have a pH that is physiologically tolerable by a patient for an infusion lasting greater than about 3 hours, or greater than about 6 hours. Liquid formulations having features of the invention include undiluted liquid formulations as well as dilutions of liquid formulations for bolus administration that are diluted with a diluent at a ratio of at least about 1:1; or at least about 1:2; or at least about 1:5; or at least about 1:10; or at least about 1:20; or at least about 1:30; or at least about 1:40; or at least about 1:50.

In embodiments of the liquid formulations having features of the invention, before dilution, a liquid formulation may include at least 0.04 mg/ml SUR-active compound or compounds in a solution comprising 40% PEG 300, 10% ethanol, and 50% water at a pH of between about pH 8.5 to about pH 9.5. In further embodiments, a liquid formulation may include at least 0.05 mg/ml SUR-active compound or compounds in a solution comprising 40% PEG 300, 10% ethanol, and 50% water at a pH of between about pH 8.5 to about pH 9.5, and including a surfactant, such as Tween 80. In a further embodiment, a liquid formulation may include at least 0.04 mg/ml SUR-active compound or compounds in a solution comprising 40% PEG 400, 10% ethanol, and 50% water at a pH of between about pH 8.5 to about pH 9.5; in embodiments, this solution may further include a surfactant, such as Tween 80.

In yet further embodiments, a liquid formulation having features of the invention may include at least 0.04 mg/ml SUR-active compound or compounds in a solution comprising 50% PEG 300, 10% ethanol, and 40% water at a pH of between about pH 8 to about pH 9; this solution may further include a surfactant, such as Tween 80. Other embodiments of the liquid formulation having features of the invention include a liquid formulation that includes at least 0.05 mg/ml SUR-active compound or compounds in a solution comprising 40% PEG 300, 10% ethanol, and 35% water at a pH of between about pH 8 to about pH 9, and optionally including a surfactant, such as 15% Tween 80.

In embodiments of the liquid formulations having features of the invention, before dilution, a liquid formulation may include at least 0.05 mg/ml Glibenclamide in a solution comprising 40% PEG 300, 10% ethanol, and 50% water at a pH of between about pH 8.5 to about pH 9.5. In further embodiments, a liquid formulation may include at least 0.05 mg/ml Glibenclamide in a solution comprising 40% PEG 300, 10% ethanol, and 50% water at a pH of between about pH 8.5 to about pH 9.5, and including Tween 80. In a further embodiment, a liquid formulation may include at least 0.05 mg/ml Glibenclamide in a solution comprising 40% PEG 400, 10% ethanol, and 50% water at a pH of between about pH 8.5 to about pH 9.5; in embodiments, this solution may further include Tween 80.

In yet further embodiments, a liquid formulation having features of the invention may include at least 0.05 mg/ml Glibenclamide in a solution comprising 50% PEG 300, 10% ethanol, and 40% water at a pH of between about pH 8 to about pH 9; this solution may further include Tween 80. Other embodiments of the liquid formulation having features of the invention include a liquid formulation that includes at least 0.05 mg/ml Glibenclamide in a solution comprising 40% PEG 300, 10% ethanol, and 35% water at a pH of between about pH 8 to about pH 9, and optionally including 15% Tween 80.

Liquid formulations having features of the invention include dilutions of the liquid formulations discussed above. Such liquid formulations may be provided using a pharmaceutically acceptable buffered solution as a diluent. The diluent may also include a sugar or a sugar alcohol. A sugar or sugar alcohol suitable for inclusion in a pharmaceutically acceptable diluent solution may be selected from glucose, fructose, mannose, galactose, arabinose, xylose, ribose, mannitol, maltose, lactose, sucrose, trehalose, raffinose, and maltotriose.

Glibenclamide Solubility

Glibenclamide (N-p-(2-[5-Chloro-2-methoxybenzamido]ethyl) benzenesulfonyl-N'-cyclohexylurea; also known as glibenclamide) is a representative and preferred SUR-active compound. The solubility of glibenclamide was tested in various solutions and at various pH. The results of these solubility experiments are presented in Table 1.

TABLE 1

Glibenclamide Solubility

| Solvent | pH | Solubility (mg/ml) |
|---|---|---|
| Water | 8.3 | 0.02 |
| pH 5 buffer | 5.3 | 0.01 |
| pH 6 buffer | 6.2 | 0.01 |
| pH 7 buffer | 7.1 | 0.01 |
| pH 8 buffer | 8.0 | 0.02 |
| pH 9 buffer | 9.0 | 0.14 |
| pH 10 buffer | 9.7 | 0.86 |
| 1% Tween 80 | 7.7 | 0.01 |
| 10% Solutol | 7.2 | 0.08 |
| 10% Cremophor | 7.2 | 0.05 |
| 2% Benzyl alcohol | 6.6 | 0.07 |
| 10% Pharmasolve | 7.6 | 0.60 |
| Ethanol, absolute | — | 2.38 |
| PEG 300 | — | 8.39 |
| PEG 400 | — | 7.55 |
| Propylene glycol | — | 1.31 |
| Tetraglycol | — | 17.88 |
| DMA | — | 247.15 |
| Glycerol | — | 0.06 |
| PEG 300/Ethanol/water 40/10/50 | 7.2 | 0.07 |
| PEG 300/DMA/water 40/10/50 | 6.9 | 0.09 |
| PEG 300/Tetraglycol/water 40/10/50 | 6.9 | 0.06 |
| 100 mM Meglumine | 10.7 | 8.12 |
| 100 mM Meglumine, pH 10 | 10.1 | 2.35 |
| PEG 300/Ethanol/200 mM Meglumine 40/10/50 | 10.5 | 13.44 |
| PEG 300/DMA/200 mM Meglumine 40/10/50 | 10.5 | 15.65 |
| PEG 300/Tetraglycol/200 mM Meglumine 40/10/50 | 10.7 | 13.93 |
| PEG 300/Ethanol/200 mM Meglumine pH 10 40/10/50 | 9.7 | 18.28 |
| PEG 300/DMA/200 mM Meglumine pH 10 40/10/50 | 9.8 | 14.65 |
| PEG 300/Tetraglycol/200 mM Meglumine pH 10 40/10/50 | 9.8 | 11.20 |

The effect of pH on solubility of SUR-active compounds was investigated further. The solubility of glibenclamide was measured at various pH levels in the presence of different amounts of the buffer meglumine in solutions containing 40% PEG 300, 10% ethanol, and 50% water. The final meglumine concentration was 10 mM, 25 mM, and 50 mM, as shown in Table 2 (which presents glibenclamide solubility solutions containing 40% PEG 300, 10% ethanol, and 50% water and meglumine buffer at various pH levels). The pH of the meglumine buffer was adjusted down from pH 11 to the target pH range of between about pH 8 to about pH 10. At nominal pH 9 (pH 8.8) a solubility of 2.7 mg/ml was obtained.

TABLE 2

Glibenclamide Solubility at Various pHs

| Nominal pH | Actual pH | Solubility mg/ml |
|---|---|---|
| PEG 300/Ethanol/20 mM Meglumine * 40%/10%/50% | | |
| 8.0 | 5.3 | 0.07 |
| 8.5 | 5.4 | 0.10 |
| 9.0 | 5.6 | 0.13 |
| 9.5 | 6.4 | 0.12 |
| 10.0 | 6.9 | 0.98 |
| PEG 300/Ethanol/50 mM Meglumine * 40%/10%/50% | | |
| 8.0 | 5.2 | 0.16 |
| 8.5 | 5.4 | 0.06 |
| 9.0 | 6.0 | 0.07 |
| 9.5 | 6.6 | 0.09 |
| 10.0 | 7.8 | 0.36 |
| PEG 300/Ethanol/100 mM Meglumine * 40%/10%/50% | | |
| 8.0 | 5.3 | 0.09 |
| 8.5 | 5.5 | 0.10 |
| 9.0 | 6.2 | 0.10 |
| 9.5 | 7.7 | 0.41 |
| 10.0 | 8.8 | 2.74 |

* final concentration of meglumine in vehicle is half that indicated i.e. 10 mM, 25 mM and 50 mM respectively.

As shown in FIGS. 1 and 2, there is a rapid increase in SUR-active compound solubility as pH increases from about pH to about pH 10. The inventors have observed that at lower pH levels, the presence of a co-solvent is has a smaller effect on SUR-active compound solubility than at higher pH levels. It appears that at higher pH levels the presence of a co-solvent improves SUR-active compound solubility over the solubility that would be obtained by higher pH alone.

Further investigation of glibenclamide solubility in polyethylene glycol/ethanol/meglumine solutions is presented in Table 3. Increasing pH is shown to increase the solubility of the glibenclamide in these experiments as well.

TABLE 3 pH after a 50-fold Dilution of Glibenclamide
1 mg/ml in PEG/Ethanol/Buffer (4/1/5)

| | Hartmann's pH 6.48 | pH 6.60 | NaCl pH 4.59 | pH 6.82 |
|---|---|---|---|---|
| Meglumine 5 mM | | | | |
| pH 8 | 6.66 | 6.55 | 6.56 | 8.21 |
| pH 9 | 6.8 | | | 8.40 |
| pH 9.5 | 6.93 | 8.49 | 8.04 | 8.71 |
| pH 10 | 8.32 | | | |
| Meglumine 10 mM | | | | |
| pH 9 | 7.37 | | 6.35 | |
| pH 10 | 8.98 | | | 9.54 |
| Diethanolamine 5 mM | | | | |
| pH 8 | 6.71 | 7.99 | 7.27 | 8.32 |
| pH 9 | 7.54 | | | 8.65 |
| pH 9.5 | 6.73 | 8.85 | 8.72 | 8.88 |
| pH 10 | 8.46 | | | |
| Diethanolamine 10 mM | | | | |
| pH 9 | 8.38 | | 8.46 | |
| pH 10 | 8.88 | | | 9.31 |

Glibenclamide Liquid Formulations

Example 1

A liquid formulation having 40% PEG 300, 10% Ethanol and 50% water, at a pH of about pH 9 (8.5-9.5) included 1 mg glibenclamide per ml. This formulation may also include a buffer, such as meglumine or diethanolamine. This formulation may also include a surfactant; for example, this solution may include Tween 80 (e.g., less than about 1 ug/ml or less than about 1 ug/mg of glibenclamide). This formulation can be stored in a refrigerator (e.g., at about 2-8° C.) or can be stored at room temperature. This formulation is suitable for dilution; for example, it may be diluted 1:1, or 1:2 for use in bolus injections. This formulation may also be diluted by larger amounts of diluent, to 1:50 for example, for administration of glibenclamide as an infusion over an extended period of time. Dilution with a buffered solution allows the reduction of the solution pH to physiological levels without causing precipitation of glibenclamide. Glibenclamide remained in solution during and following dilution of this solution 1:50 with Hartman's solution.

pH after a 50-fold Dilution of Glibenclamide
1 mg/ml in PEG/Ethanol/Buffer (4/1/5)

| | Dilution into Hartmann's (pH 6.48) | |
|---|---|---|
| | Expt1 | Expt 2 |
| Meglumine 5 mM | | |
| pH 8 | 6.66 | — |
| pH 8.5 | — | 6.64 |
| pH 9 | 6.8 | 6.96 |
| pH 9.5 | 6.93 | 7.68 |
| Diethanolamine 5 mM | | |
| pH 8 | 6.71 | — |
| pH 8.5 | — | 6.82 |
| pH 9 | 7.54 | 7.29 |
| pH 9.5 | 6.73 | 8.37 |

Example 2

A further liquid formulation containing glibenclamide or tolbutamide includes 50% PEG 300, 10% Ethanol and 40% Water, and has a small quantity of Tween 80<<1 ug/mg glibenclamide), at pH 8.4. This solution may be diluted by about 1:2 or 1:3. This formulation may also include a buffer, such as meglumine or diethanolamine.

Example 3

A further liquid formulation containing glibenclamide or tolbutamide includes 40% PEG 300, 15% Tween 80, 10% Ethanol and 35% water, and 1 mg/ml glibenclamide.

Example 4

A further liquid formulation containing glibenclamide or tolbutamide includes 40% PG, 10% Ethanol and 50% water. This solution may also include a surfactant, and may be diluted by about 1:2 or 1:3. This formulation may also include a buffer, such as meglumine or diethanolamine.

Example 5

A further liquid formulation containing glibenclamide or tolbutamide includes 50% PG, 10% Ethanol and 40% Water, and has a small quantity of Tween 80 (<1 ug/mg glibenclamide), at pH 8.4. This solution may be diluted by about 1:2 or 1:3. This formulation may also include a buffer, such as meglumine or diethanolamine.

Example 6

A further liquid formulation containing glibenclamide or tolbutamide includes 40% PG, 15% Tween 80, 10% Ethanol and 35% water.

Example 7

A further liquid formulation containing glibenclamide or tolbutamide includes 40% PEG 400, 10% Ethanol and 50% water. This solution may also include a surfactant, and may be diluted by about 1:2 or 1:3. This formulation may also include a buffer, such as meglumine or diethanolamine.

Example 8

A further liquid formulation containing glibenclamide or tolbutamide includes 50% PEG 400, 10% Ethanol and 40% Water, and has a small quantity of Tween 80 (<1 ug/ml), at pH 8.4. This solution may be diluted by about 1:2 or 1:3. This formulation may also include a buffer, such as meglumine or diethanolamine.

Example 9

A further liquid formulation containing glibenclamide or tolbutamide includes 40% PEG 400, 15% Tween 80, 10% Ethanol and 35% water.

Example 10

A further liquid formulation containing glibenclamide or tolbutamide includes 70% Cremophor ELP and 30% Ethanol.

Example 11

Further liquid formulations are as follows:

| Ingredient | SP06092-01 | SP06092-02 | SP06092-03 | SP06092-04 |
|---|---|---|---|---|
| Glibenclamide | 1.0 mg | 1.0 mg | 1.0 mg | 1.0 mg |
| Meglumine | 0.976 mg (5 mM) | — | 1.952 mg (10 mM) | — |
| Diethanolamine | — | 0.526 mg (5 mM) | — | — |
| Ethanol | 0.1 ml | 0.1 ml | 0.1 ml | 0.2 ml |
| PEG 300 | 0.4 ml | 0.4 ml | 0.4 ml | to 1.0 ml |
| NaOH/HCl | qs to pH 9.0 | qs to pH 9.0 | qs to pH 9.5 | — |
| Water for Irrigation | to 1.0 ml | to 1.0 ml | to 1.0 ml | — |

The formulation SP06092-04 does not contain water, and is diluted prior to use so as to replicate any of the aforementioned buffered, unbuffered, pH adjusted, or non-pH adjusted formulations.

Dosages

In one embodiment, the liquid formulations provide solutions having a relatively high concentration of a SUR-active compound (e.g., greater than about 0.05 mg/ml). In embodiments, the concentration of a SUR-active compound may be greater than about 0.1 mg/ml, or greater than about 0.2 mg/ml, or greater than about 0.5 mg/ml, or greater than about 1 mg/ml, or greater than about 2 mg/ml, or greater than about 5 mg/ml, or greater than about 10 mg/ml, or greater than about 20 mg/ml. In embodiments in which the liquid formulations comprise more than one SUR-active compound, liquid formulations having features of the invention have relatively high concentrations of SUR-active compounds (e.g., greater than about 0.05 mg/ml). In embodiments, the combined concentrations of the SUR-active compounds may be greater than about 0.1 mg/ml, or greater than about 0.2 mg/ml, or greater than about 0.5 mg/ml, or greater than about 1 mg/ml, or greater than about 2 mg/ml, or greater than about 5 mg/ml, or greater than about 10 mg/ml, or greater than about 20 mg/ml. In embodiments, the individual concentration of one or more of the SUR-active compounds may be greater than about 0.1 mg/ml, or greater than about 0.2 mg/ml, or greater than about 0.5 mg/ml, or greater than about 1 mg/ml, or greater than about 2 mg/ml, or greater than about 5 mg/ml, or greater than about 10 mg/ml, or greater than about 20 mg/ml.

Dilutions

Experiments investigating the effect of dilution of relatively high concentrations of SUR-active compounds were performed. Solutions of 2 mg/ml glibenclamide were made with either 0.9% NaCl or 5% glucose in 100 mM meglumine buffer. These solutions were diluted as follows with each of these diluents (0.9% NaCl and 5% glucose solutions): 1 in 2; 1 in 4; 1 in 5; 1 in 10; 1 in 20; and 1 in 50. There was no precipitation with any of these dilutions.

The solubility of SUR-active compounds in fluid suitable for infusion into a patient was investigated. The solubility of glibenclamide was determined by high pressure liquid chromatography (HPLC) in a variety of infusion fluids. Excess glibenclamide was shaken with the vehicle for 24 hours at ambient temperature and the glibenclamide content of the supernatant determined by HPLC.

The following infusion vehicles were assessed in these experiments:

1.) 0.9% NaCl at the lowest end of the pH specification (pH 4.5) containing a 50-fold dilution of the PEG/ethanol/meglumine 10 mM pH 9.0 formulation.

2.) 0.9% NaCl at the lowest end of the pH specification (pH 4.5) containing a 50-fold dilution of the PEG/ethanol/diethanolamine 10 mM pH 9.0 formulation.

3.) 0.9% NaCl at the lowest end of the pH specification (pH 4.5) containing a 50-fold dilution of the PEG/ethanol/TRIS 10 mM pH 9.0 formulation.

4.) 0.9% NaCl at the lowest end of the pH specification (pH 4.5).

5.) 0.9% NaCl at the highest end of the pH specification (pH 7.0).

6.) 0.9% NaCl 'as is' (pH 5.8).

7.) 0.9% NaCl at the lowest end of the pH specification (pH 4.5) containing a 50-fold dilution of the PEG/ethanol formulation (without buffer or pH adjustment).

8.) 0.9% NaCl at the highest end of the pH specification (pH 7.0) containing a 50-fold dilution of the PEG/ethanol formulation (without buffer or pH adjustment).

For example, glibenclamide solubility in solutions having sodium chloride, polyethylene glycol, ethanol, with and without buffer (where the buffers investigated were 10 mM meglumine, 10 mM diethanolamine, and 10 mM tris(hydroxymethyl) aminomethane (TRIS)) is shown in Table 4.

TABLE 4

Glibenclamide Solubility 50-Fold Dilution

| | Actual pH | Solubility (mg/ml) |
|---|---|---|
| NaCl at pH 4.5 + PEG/EtOH/Meglumine 10 mM, pH 9.0 | 7.92 | 0.15 |
| NaCl at pH 4.5 + PEG/EtOH/Diethanolamine 10 mM, pH 9.0 | 8.19 | 0.13 |
| NaCl at pH 4.5 + PEG/EtOH/TRIS 10 mM, pH 9.0 | 7.89 | 0.15 |
| NaCl at pH 4.5 | 7.72 | 0.08 |
| NaCl at pH 7.0 | 7.75 | 0.12 |
| NaCl 'as is' | 7.80 | 0.15 |
| NaCl at pH 4.5 + PEG/EtOH, no buffer | 7.64 | 0.10 |
| NaCl at pH 7.0 + PEG/EtOH, no buffer | 7.90 | 0.14 |

The pH of the supernatant was also measured in these experiments; it was found that all the samples ended up within a pH range of about pH 7.6 to pH 8.2.

In further experiments, a number of formulations were diluted into Hartmann's solution (50-fold dilution). It was found that Hartmann's solution performed better than normal saline, resulting in a lower final pH when infusion fluids of similar starting pH are compared. For either saline or Hartmann's solutions, it was found that, where the initial, concentrated solution had a pH of 10, the resulting pH of the diluted solution was typically greater than pH 8. This was found even for experiments in which the concentration of buffer was reduced to 5 mM.

In order to determine whether the pH of the concentrated solution might be lowered while maintaining SUR-active compound solubility, the pH a concentrate was reduced. A clear solution was obtained at pH levels down to pH 7.2. Haziness of the solution was observed at pH 6.9.

In order to determine the final pH of diluted solutions resulting from high pH solutions having high concentrations of SUR-active compounds, measurements of the pH of glibenclamide solutions at various levels of dilution were made. High concentration glibenclamide solutions (1 mg/ml glibenclamide in 40% PEG, 10% ethanol, 50% water) including either 5 mM meglumine or 5 mM diethanolamine buffers were diluted with 50-fold using pH 6.48 Hartmann's solution (1:50 dilution). Initial pH varied from pH 8 to pH 9. The results are presented in Table 5.

TABLE 5 pH after a 50-fold Dilution of Glibenclamide 1 mg/ml in PEG/Ethanol/Buffer (4/1/5)

| | Dilution into Hartmann's (pH 6.48) | |
|---|---|---|
| | Expt1 | Expt2 |
| Meglumine 5 mM | | |
| pH 8 | 6.66 | — |
| pH 8.5 | — | 6.64 |
| pH 9 | 6.8 | 6.96 |
| pH 9.5 | 6.93 | 7.68 |
| Diethanolamine 5 mM | | |
| pH 8 | 6.71 | — |
| pH 8.5 | — | 6.82 |
| pH 9 | 7.54 | 7.29 |
| pH 9.5 | 6.73 | 8.37 |

TABLE 5-continued pH after a 50-fold Dilution of Glibenclamide 1 mg/ml in PEG/Ethanol/Buffer (4/1IS)

| | Hartmann's | NaCl | | |
|---|---|---|---|---|
| | pH 6.48 | pH 6.60 | pH 4.59 | pH 6.82 |
| Meglumine 5 mM | | | | |
| pH 8 | 6.66 | 6.55 | 6.56 | 8.21 |
| pH 9 | 6.8 | | | 8.40 |
| pH 9.5 | 6.93 | 8.49 | 8.04 | 8.71 |
| pH 10 | 8.32 | | | |
| Meglumine 10 mM | | | | |
| pH 9 | 7.37 | | 6.35 | |
| pH 10 | 8.98 | | | 9.54 |
| Diethanolamine 5 mM | | | | |
| pH 8 | 6.71 | 7.99 | 7.27 | 8.32 |
| pH 9 | 7.54 | | | 8.65 |
| pH 9.5 | 6.73 | 8.85 | 8.72 | 8.88 |
| pH 10 | 8.46 | | | |
| Diethanolamine 10 mM | | | | |
| pH 9 | 8.38 | | 8.46 | |
| pH 10 | 8.88 | | | 9.31 |

Example 12 Stability

Glibenclamide stability was investigated by storing several formulations under different conditions for long periods of time. In particular, glibenclamide formulations suitable for injection were stored for up to six months and stability data for these formulations was obtained over that period of time.

This study assessed the relative stability of 4 batches of glibenclamide formulations suitable for injection. The following studies were conducted.

| Study No. | Formulation Description |
|---|---|
| SP06092-01 | Lead Formulation - Glibenclamide 1.0 mg/ml at pH 9 with meglumine buffer 5 mM |
| SP06092-02 | Back-up Formulation - Glibenclamide 1.0 mg/ml at pH 9 with diethanolamine buffer 5 mM |
| SP06092-03 | Back-up Formulation-Glibenclamide 1.0 mg/ml at pH 9.5 with meglumine buffer 10 mM |
| SP06092-04 | Back-up Formulation - Glibenclamide 1.0 mg/ml (non-aqueous formulation) |

Description of Glibenclamide Formulations
Composition of Glibenclamide Injections for Stability Evaluation

| Ingredient | SP06092-01 | SP06092-02 | SP06092-03 | SP06092-04 |
|---|---|---|---|---|
| Glibenclamide | 1.0 mg | 1.0 mg | 1.0 mg | 1.0 mg |
| Meglumine | 0.976 mg | — | 1.952 mg | — |
| Diethanolamine | — | 0.526 mg | — | — |
| Ethanol | 0.1 ml | 0.1 ml | 0.1 ml | 0.2 ml |
| PEG 300 | 0.4 ml | 0.4 ml | 0.4 ml | to 1.0 ml |
| NaOH/HCl | qs to pH 9.0 | qs to pH 9.0 | qs to pH 9.5 | — |
| Water for Irrigation | to 1.0 ml | to 1.0 ml | to 1.0 ml | — |

Method of Preparation

The ethanol and PEG 300 were measured into a suitable vessel and the glibenclamide added. The mixture was stirred until the glibenclamide had dissolved.

As appropriate, the buffer salt was dissolved in approximately 40% of the batch volume of water. Once dissolved the buffer solution was added to the PEG/ethanol solution of glibenclamide with stirring. The pH of this solution was measured and adjusted to pH 9.0±0.1 (or pH 9.5±0.1 as appropriate) with sodium hydroxide or hydrochloric acid solutions. The solutions were brought to their final volume with further water for irrigation and the pH was re-measured and adjusted as required.

The solutions were sterilized by passing through a 0.2 μm filter. Aliquots of 5 ml were filled into pre-sterilized 5 ml vials and sealed with a pre-sterilized stopper.

Testing Protocol

The glibenclamide injections were stored and tested according to the schedules below, in which the symbols X, Y, and Z have the following meanings:

X Appearance, pH, assay and related substances
Y Appearance, pH, assay and related substances
Z Appearance, assay and related substances.

| Study SP06092-01 | | | | | |
|---|---|---|---|---|---|
| | Initial | 1M | 2M | 3M | 6M |
| 2-8° | X | X | X | X | (X) |
| 25° C./60% RH | — | X | X | X | (X) |
| 40° C./75% RH | — | X | X | X | (X) |
| ICH Light | | | X | | |

| Study SP06092-02 and SP06092-03 | | | | | |
|---|---|---|---|---|---|
| | Initial | 1M | 2M | 3M | 6M |
| 2-8° C. | Y | Y | Y | Y | (Y) |
| 25° C./60% RH | — | Y | Y | Y | (Y) |
| 40° C./75% RH | — | Y | Y | Y | (Y) |
| ICH Light | | | Y | | |

| Study SP06092-04 | | | | | |
|---|---|---|---|---|---|
| | Initial | 1M | 2M | 3M | 6M |
| 2-8° C. | Z | (Z) | (Z) | (Z) | (Z) |
| 25° C./60% RH | — | (Z) | (Z) | (Z) | (Z) |
| 40° C./75% RH | — | (Z) | (Z) | (Z) | (Z) |
| ICH Light | | | (Z) | | |

All storage cabinets were continually monitored for temperature and humidity using calibrated probes. After removal from long-term storage, all samples were stored at 2-8° C. protected from light while awaiting analysis.

At each time point, 2 vials of glibenclamide injections will be removed from the storage cabinet from the appropriate conditions and allowed to equilibrate to ambient temperature. This will be used to perform the analyses described above and will be stored under normal laboratory conditions throughout the duration of the analyses.

The formulations were inspected visually for appearance and for the presence of particulates. The pH of duplicate samples from separate vials was measured to determine formulation pH and to track changes, if any, over the course of time during the stability experiments. Results of glibenclamide stability experiments are presented in FIG. 3, which shows glibenclamide stability in various formulations.

FIG. 3A shows glibenclamide stability at a concentration of 1 mg/ml at pH 9, with 5 mM meglumine, when stored at 2-8° C. FIG. 3B shows glibenclamide stability at a concentration of 1 mg/ml at pH 9, with 5 mM meglumine, when stored at 25° C. and 60% relative humidity. FIG. 3C shows glibenclamide stability at a concentration of 1 mg/ml at pH 9, with 5 mM meglumine, when stored at 40° C. and 75% relative humidity. FIG. 3D shows glibenclamide stability at a concentration of 1 mg/ml at pH 9, with 5 mM diethanolamine, when stored at 2-8° C. FIG. 3E shows glibenclamide stability at a concentration of 1 mg/ml at pH 9, with 5 mM diethanolamine, when stored at 25° C. and 60% relative humidity. FIG. 3F shows glibenclamide stability at a concentration of 1 mg/ml at pH 9, with 5 mM diethanolamine, when stored at 40° C. and 75% relative humidity. FIG. 3G shows glibenclamide stability at a concentration of 1 mg/ml at pH 9.5, with 10 mM meglumine, when stored at 2-8° C. FIG. 3H shows glibenclamide stability at a concentration of 1 mg/ml at pH 9.5, with 10 mM meglumine, when stored at 25° C. and 60% relative humidity. FIG. 3I shows glibenclamide stability at a concentration of 1 mg/ml at pH 9.5, with 10 mM meglumine, when stored at 40° C. and 75% relative humidity. FIG. 3J shows glibenclamide stability at a concentration of 1 mg/ml in a non-aqueous formulation, when stored at 25° C. and 60% relative humidity.

As shown in FIGS. 3A, 3B, and 3C, for example, there appeared to be some hydrolysis of glibenclamide in the 1 mM glibenclamide formulation with 5 mM meglumine at pH 9 when stored at elevated temperatures. However, surprisingly, such hydrolysis was not seen in the refrigerated samples stored at 2-8° C., and the glibenclamide remained in solution at these temperatures.

Methods of Use

The liquid formulations disclosed herein may be used to administer SUR-active compounds to patients in need of such compounds. For example, a patient suffering from stroke; brain trauma; heart attack leading to brain hypoxia, brain ischemia or brain hypoxia/ischemia; spinal cord injury; or other disorder leading to neural cell swelling or to brain swelling, would benefit from administration of a SUR-active compound via a liquid formulation disclosed herein. Concentrated formulations having greater than about 0.05 mg/ml of a SUR-active compound, such as glibenclamide or tolbutamide, may be administered as a bolus infusion to a vein or artery of a patient in need of such treatment, effective to provide an initial effective dose of the compound. A bolus infusion may provide greater than about 0.1 mg/ml, or greater than about 0.5 mg/ml, or greater than about 1 mg/ml, or greater than about 5 mg/ml, or greater than about 10 mg/ml, or greater than about 20 mg/ml of a SUR-active compound. A bolus infusion may be an infusion lasting for a period of time of up to 15 minutes, or up to 30 minutes, or up to about one hour, or up to about 3 hours. A SUR-active compound may be administered to a patient at lower doses as well, and typically via steady infusion of drug over an extended period of time, effective to maintain an effective dose of the compound to provide treatment to the patient. A long-term infusion may provide a SUR-active compound at a concentration of less than about 0.01 mg/ml, or of about 0.01 mg/ml, or of about 0.02 mg/ml, or of about 0.03 mg/ml, or of about 0.04 mg/ml, or of greater than about 0.04 mg/ml of a SUR-active compound. A long-term infusion may be an infusion lasting for a period of time of about 3 hours; or may be for a period of time of about 6 hours; or may be for a period of time of about 12 hours; or may be for a period of time of about a day; or may be for a period of time of about 2 days; or may be for a period of time of about 5 days; or may be for a period of time of about one week; or may be for a period of time of about two weeks; or may be for a period of time of about one month; or may be for another time period.

In addition, a patient suffering from a disorder of blood glucose levels will benefit from administration of a SUR-active compound via a liquid formulation disclosed herein.

The methods disclosed herein provide methods of providing a concentrated liquid formulation of a SUR-active compound containing a significant amount of water, comprising the step of dissolving a SUR-active compound in a solution containing a solvent, a co-solvent, and optionally a surfactant. In embodiments of the methods of the invention, the solvent is ethanol. In embodiments of the methods of the invention, the co-solvent is a polyalkylene glycol. In further embodiments of the methods of the invention, the liquid formulation includes a buffer. In embodiments of the methods of the invention, the buffer is selected from meglumine and diethanolamine. In embodiments of the methods, the pH of the liquid formulation is between about pH 8.5 and about pH 9.5

The methods disclosed herein provide methods of providing a liquid formulation of a SUR-active compound containing a significant amount of water, comprising the step of diluting a concentrated liquid formulation of a SUR-active compound with a pharmaceutically acceptable solution containing water, wherein the diluting step does not produce precipitation of the SUR-active compound. In embodiments of the methods disclosed herein, the pharmaceutically acceptable solution containing water further includes a buffer. In embodiments of the methods, the pH of the diluted liquid formulation is between about pH 7.0 and about pH 8.5.

Kits

A kit may be provided which includes a SUR-active compound dissolved in a liquid formulation having features of the invention in a suitable container and includes instructions for the use of the novel liquid formulation according to the methods disclosed herein. Preferred kits provide the liquid formulations in sterile containers, as is known in the art. A kit having features of the invention may also include a diluent, such as Hartmann's solution, in a suitable container, and including instructions for the use of the novel liquid formulation according to the methods disclosed herein. In preferred embodiments of the kits, the volume of the diluent provided is greater than the volume of the SUR-active compound-containing liquid formulation provided. For example, a kit having features of the invention may provide 50 times the volume of a diluent such as Hartmann's solution as compared to the volume of the liquid formulation containing dissolved SUR-active compound. For non-aqueous solutions, kits may further contain buffered, unbuffered, pH adjusted, or non-pH adjusted formulations which do not include the active ingredient and which may be used to dilute the non-aqueous solutions.

In embodiments, a kit may be provided which includes a vial of a SUR-active compound in a dry form, such as, e.g., a powdered form (including, e.g., micronized or non micronized powder, or other dry powder). The kit may further include a vial of diluent suitable for dilution of the powdered SUR-active compound to provide, upon mixing, a liquid formulation containing the SUR-active compound. The diluent may be water; or may include water and alcohol; or may include water, PEG and alcohol; or may be or include other liquid, including non-aqueous liquids. In embodiments, the diluent may have a pH of 7.4 or greater. In further embodiments, the diluent may have a pH of 7.4 or greater and may be buffered. The buffer in such a buffered solution may be at a concentration within in the range of about 1 mM to about 100 mM; for example, the buffer may have a concentration of about 5 mM or a concentration of about 10 mM. In embodiments, the buffer is meglumine or diethanolamine.

For example, a kit may be provided which includes a vial of glibenclamide in a powdered form (including, e.g., micronized or non micronized powder, or other dry powder) packaged with a vial of diluent. The diluent may be water; or may include water and alcohol; or may include water, PEG and alcohol; or may be or include other liquid, including nonaqueous liquids. In embodiments, the diluent may have a pH of 7.4 or greater. In further embodiments, the diluent may have a pH of 7.4 or greater and may be buffered. The buffer in such a buffered solution may be at a concentration within the range of about 1 mM to about 100 mM; for example, the buffer may have a concentration of about 5 mM or a concentration of about 10 mM. In embodiments, the buffer is meglumine or diethanolamine.

In further embodiments, a kit may include a SUR-active compound and a buffer salt in a powdered form (including, e.g., micronized or non micronized powder, or other dry powder). The SUR-active compound and the buffer salt may be provided in proportions of, for example, 4:1 w/w SUR-active compound:buffer salt; 2:1 w/w SUR-active compound:buffer salt; 1:1 w/w SUR-active compound:buffer salt; 0.5:1 w/w SUR-active compound:buffer salt; 0.25:1 w/w SUR-active compound:buffer salt; or other proportions. In embodiments, the buffer salt is a salt of meglumine or diethanolamine. The kit may further include a vial of diluent suitable for dilution of the powdered SUR-active compound and buffer salt to provide, upon mixing, a liquid formulation containing the SUR-active compound in a buffered solution. The diluent may be water; or may include water and alcohol; or may include water, PEG and alcohol; or may be or include other liquid, including non-aqueous liquids. The diluent need not be buffered, as the powder includes a buffer salt. The resulting mixture of powder with diluent preferably has a pH of between about pH 8.5 and about pH 11.5. The desired resulting pH depends upon the proportion of SUR-active compound to buffer salt, where that proportion is chosen to provide the desired resulting pH.

Following dilution of a powder of a SUR-active compound and buffer salt with such a diluent, the resulting dilution mixture may be added to water to provide an aqueous formulation suitable for injection. For example, such a dilution mixture may be used to provide an aqueous formulation for injection of about 0.05 mg/ml to about 20 mg/ml of a SUR-active compound for bolus injection, or infusion (e.g., via a syringe pump), or for other method of administration to a patient. Such a dilution mixture may also be used to provide an aqueous formulation for addition to a buffered solution, such as a physiological saline, Ringer's solution, Hartmann's solution, or other buffered aqueous solution, suitable for continuous infusion into a patient, or for other suitable mode of administration. Thus, a powder including a SUR-active compound and a buffer salt may be provided in kit form to provide the ingredients for a pharmaceutical formulation suitable for addition to a further diluent solution, such as, for example, a buffered aqueous solution. This embodiment differs from the previously described embodiment which provides a SUR-active compound and a diluent, which is also suitable for addition to a further diluent solution, in that the present embodiment further includes a buffer salt with the SUR-active compound.

For example, a kit may include a glibenclamide and a buffer salt in a powdered form (including, e.g., micronized or non micronized powder, or other dry powder). The glibenclamide and the buffer salt may be provided in proportions of, for example, 4:1 w/w glibenclamide:buffer salt; 2:1 w/w glibenclamide:buffer salt; 1:1 w/w glibenclamide: buffer salt; 0.5:1 w/w glibenclamide:buffer salt; 0.25:1 w/w glibenclamide:buffer salt; or other proportions. In embodiments, the buffer salt is a salt of meglumine or diethanolamine. The kit may further include a vial of diluent suitable for dilution of the powdered glibenclamide and buffer salt to provide, upon mixing, a liquid formulation containing the glibenclamide in a buffered solution. The diluent may be water; or may include water and alcohol; or may include water, PEG and alcohol; or may be or include other liquid, including non-aqueous liquids. The diluent need not be buffered, as the powder includes a buffer salt. The resulting mixture of powder with diluent preferably has a pH of between about pH 8.5 and about pH 11.5. The desired resulting pH depends upon the proportion of glibencl amide to buffer salt, where that proportion is chosen to provide the desired resulting pH.

Following dilution of the glibenclamide and buffer powder, the resulting dilution mixture may be added to water to provide an aqueous formulation suitable for injection, e.g., a formulation having about 0.05 mg/ml to about 20 mg/ml glibenclamide. Such glibenclamide and buffer formulations are suitable for bolus injection, or infusion (e.g., via a syringe pump), or for other method of administration to a patient. Such glibenclamide and buffer formulations are also suitable for addition to a buffered solution, such as a physiological saline, Ringer's solution, Hartmann's solution, or other buffered aqueous solution, suitable for continuous infusion into a patient, or for other suitable mode of administration.

All patents, patent applications, and scientific articles cited herein, both supra and infra, are hereby incorporated by reference in their entireties.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A stable liquid formulation suitable for parenteral administration to a patient, comprising:
    10 mM to 50 mM meglumine;
    glibenclamide or a pharmaceutically acceptable salt thereof at a concentration of about 0.5 mg/ml to about 1 mg/ml;
    a pharmaceutically acceptable infusion solution comprising water, a pharmaceutically acceptable base, and a sugar alcohol;
    said liquid formulation has a pH of about pH 9 or higher and is formulated for parenteral administration, wherein the glibenclamide or pharmaceutically acceptable salt thereof has stability and solubility properties such that it does not precipitate out of the solution during or following dilution or when frozen or refrigerated, and
    wherein said formulation has stability and solubility properties such that it is stable upon storage for six months, and
    wherein said formulation has stability and solubility properties such that it remains free from visible particles upon storage for at least one month.

2. The liquid formulation of claim 1, wherein said pharmaceutically acceptable liquid infusion solution comprises mannitol.

3. The liquid formulation of claim 1 which has a pH greater than about pH 9.5.

4. The liquid formulation of claim 1, further comprising a buffer.

5. The liquid formulation of claim 1, further comprising an alcohol.

6. The liquid formulation of claim 5, wherein said alcohol is ethyl alcohol.

7. The liquid formulation of claim 1, further comprising a co-solvent.

8. The liquid formulation of claim 1, further comprising a surfactant.

9. The liquid formulation of claim 1, further comprising an alcohol and a co-solvent.

10. The liquid formulation of claim 9, further comprising a surfactant.

11. The liquid formulation of claim 9, wherein said alcohol comprises ethyl alcohol.

12. The liquid formulation of claim 9, wherein said co-solvent comprises a co-solvent selected from propylene glycol and polyalkylene glycol.

13. The liquid formulation of claim 12, wherein said co-solvent is selected from propylene glycol (PG), polyethylene glycol (PEG), polybutylene glycol, and polypropylene glycol.

14. The liquid formulation of claim 12, wherein said polyalkylene glycol comprises PEG 300.

15. The liquid formulation of claim 12, wherein said polyalkylene glycol comprises PEG 400.

16. The liquid formulation of claim 12, wherein the co-solvent comprises propylene glycol (PG).

17. The liquid formulation of claim 1, comprising glibenclamide at a concentration of about 1 mg/mL.

18. The liquid formulation of claim 1, wherein the formulation is formulated for intravenous or intra-arterial delivery and is in a vial suitable for intravenous or intra-arterial delivery.

19. The liquid formulation of claim 1, wherein the formulation is formulated for injection and is in a vial suitable for injection.

20. The liquid formulation of claim 1, further comprising propylene glycol (PG) and ethyl alcohol.

21. The liquid formulation of claim 20, wherein the propylene glycol (PG) and ethyl alcohol are present at a combined weight of at least 50 wt % of a liquid formulation in which the glibenclamide is dissolved.

22. The liquid formulation of claim 1, further comprising polyethylene glycol and ethyl alcohol.

23. The liquid formulation of claim 22, wherein the polyethylene glycol and ethyl alcohol are present at a combined weight of at least 50 wt % of a liquid formulation in which the glibenclamide is dissolved.

24. The liquid formulation of claim 1, wherein the formulation does not contain propylene glycol and polyalkylene glycols.

* * * * *